(12) United States Patent
Bonnefin et al.

(10) Patent No.: US 11,286,601 B2
(45) Date of Patent: Mar. 29, 2022

(54) PROCESSING OF CHEMICALLY MODIFIED CELLULOSIC FIBRES

(71) Applicant: CONVATEC TECHNOLOGIES INC., Las Vegas, NV (US)

(72) Inventors: Wayne Lee Bonnefin, Flintshire (GB); Lucy Louisa Ballamy, Flintshire (GB); Sarah Wroe, Flintshire (GB); David Parsons, Flintshire (GB); Garry Storey, Flintshire (GB); Joseph Thompson, Flintshire (GB)

(73) Assignee: CONVATEC TECHNOLOGIES, INC., Las Vegas, NV (US)

( * ) Notice: Subject to any disclaimer, the term of this patent is extended or adjusted under 35 U.S.C. 154(b) by 0 days.

(21) Appl. No.: 16/806,255

(22) Filed: Mar. 2, 2020

(65) Prior Publication Data

US 2020/0299865 A1 Sep. 24, 2020

Related U.S. Application Data (63) Continuation of application No. 14/654,498, filed as application No. PCT/GB2013/053374 on Dec. 20, 2013, now abandoned.

(30) Foreign Application Priority Data

Dec. 20, 2012 (GB) ..................................... 1223408
May 15, 2013 (GB) ..................................... 1308774

(51) Int. Cl.
*A61F 13/00* (2006.01)
*D06B 1/00* (2006.01)
(Continued)

(52) U.S. Cl.
CPC .......... *D06B 1/00* (2013.01); *A61F 13/00012* (2013.01); *A61F 13/00063* (2013.01);
(Continued)

(58) Field of Classification Search
None
See application file for complete search history.

(56) References Cited

U.S. PATENT DOCUMENTS

| 2,396,514 A | 3/1946 | Kreidl et al. |
| 2,785,106 A | 3/1957 | Mendelson |

(Continued)

FOREIGN PATENT DOCUMENTS

| AU | 2013366038 A1 | 7/2015 |
| CN | 101076251 A | 11/2007 |

(Continued)

OTHER PUBLICATIONS

Hurlow J, Blanz E, Gaddy J. Clinical investigation of biofilm in non-healing wounds by high resolution microscopy techniques. J Wound Care. 2016; 25(suppl 9): S11-S22.
(Continued)

*Primary Examiner* — Kim M Lewis
(74) *Attorney, Agent, or Firm* — Taft Stettinius & Hollister LLP; Ryan O. White; Derek B. Lavender (57) ABSTRACT

A chemically modified cellulosic fibre or filament having a moisture content of at least 7% by weight obtained by a process comprising the steps of (i) obtaining cellulosic fibres or filament and chemically modifying the cellulose by substitution to increase its absorbency; (ii) washing the fibres after step (i) in a mixture comprising water and up to 99% by weight of water-miscible organic solvent; (iii) drying the fibres to a moisture content of at least 7% by weight.

19 Claims, 1 Drawing Sheet

(51) Int. Cl.
*D01F 2/24* (2006.01)
*D21H 13/02* (2006.01)
*D01G 15/00* (2006.01)
*B65B 55/02* (2006.01)
*A61L 15/28* (2006.01)
*D04H 1/46* (2012.01)
*D06M 13/278* (2006.01)
*A61L 15/42* (2006.01)
*D06M 13/21* (2006.01)
*D06M 11/38* (2006.01)
*D04H 1/4258* (2012.01)
*A61F 13/02* (2006.01)
*D06M 101/06* (2006.01)

(52) U.S. Cl.
CPC .......... *A61F 13/0276* (2013.01); *A61L 15/28* (2013.01); *A61L 15/42* (2013.01); *B65B 55/02* (2013.01); *D01F 2/24* (2013.01); *D01G 15/00* (2013.01); *D04H 1/4258* (2013.01); *D04H 1/46* (2013.01); *D06M 11/38* (2013.01); *D06M 13/21* (2013.01); *D06M 13/278* (2013.01); *D21H 13/02* (2013.01); *A61F 2013/0091* (2013.01); *A61F 2013/00936* (2013.01); *D06M 2101/06* (2013.01)

(56) References Cited

U.S. PATENT DOCUMENTS

| | | |
|---|---|---|
| 3,061,469 A | 10/1962 | Manowitz et al. |
| 3,092,552 A | 6/1963 | Romans |
| 4,258,056 A | 3/1981 | Lentsch |
| 4,344,324 A | 8/1982 | Langer |
| 4,612,337 A | 9/1986 | Fox, Jr. et al. |
| 4,655,758 A | 4/1987 | Ring et al. |
| 4,728,323 A | 3/1988 | Matson |
| 4,829,129 A | 5/1989 | Kelley |
| 4,889,654 A | 12/1989 | Mason et al. |
| 4,906,100 A | 3/1990 | Rice et al. |
| 4,973,848 A | 11/1990 | Kolobanov et al. |
| 5,064,652 A | 11/1991 | Bay |
| 5,326,567 A | 7/1994 | Capelli |
| 5,340,924 A | 8/1994 | Tomita et al. |
| 5,407,656 A | 4/1995 | Roozdar |
| 5,527,534 A | 6/1996 | Myhling |
| 5,567,495 A | 10/1996 | Modak et al. |
| 5,616,347 A | 4/1997 | Alliger et al. |
| 5,662,913 A | 9/1997 | Capelli |
| 5,709,870 A | 1/1998 | Yoshimura et al. |
| 5,731,083 A | 3/1998 | Bahia et al. |
| 5,744,151 A | 4/1998 | Capelli |
| 5,744,155 A | 4/1998 | Friedman et al. |
| 5,762,620 A | 6/1998 | Cartmell et al. |
| 5,820,918 A | 10/1998 | Ronan et al. |
| 5,848,995 A | 12/1998 | Walder |
| 5,860,947 A | 1/1999 | Stamler |
| 5,998,488 A | 12/1999 | Shinohara et al. |
| 6,075,177 A † | 6/2000 | Bahia |
| 6,207,601 B1 | 3/2001 | Maurer et al. |
| 6,238,691 B1 | 5/2001 | Huang |
| 6,290,496 B1 | 9/2001 | Azar et al. |
| 6,413,556 B1 | 7/2002 | Bathurst et al. |
| 6,468,965 B1 | 10/2002 | Cutler |
| 6,548,730 B1 | 4/2003 | Patel et al. |
| 6,555,508 B1 | 4/2003 | Paul et al. |
| 6,605,751 B1 | 8/2003 | Gibbins et al. |
| 6,669,981 B2 | 12/2003 | Parsons et al. |
| 6,750,262 B1 | 6/2004 | Haehnle et al. |
| 6,753,063 B1 | 6/2004 | Pung et al. |
| 7,033,511 B2 | 4/2006 | Zawada et al. |
| 7,267,828 B2 | 9/2007 | Parsons et al. |
| 8,637,072 B2 | 1/2014 | Kershaw et al. |
| 9,149,035 B2 | 10/2015 | Percival et al. |
| 10,016,537 B2 | 7/2018 | Menon et al. |
| 10,046,096 B2 | 8/2018 | Askem et al. |
| 10,076,447 B2 | 9/2018 | Barta et al. |
| 10,076,587 B2 | 9/2018 | Locke et al. |
| 10,143,784 B2 | 12/2018 | Walton et al. |
| 10,426,670 B2 | 10/2019 | von Blucher et al. |
| 10,426,747 B2 | 10/2019 | Johnson |
| 10,426,874 B2 | 10/2019 | Chien et al. |
| 10,426,875 B2 | 10/2019 | Blott et al. |
| 10,426,938 B2 | 10/2019 | Locke et al. |
| 10,434,015 B2 | 10/2019 | Taylor et al. |
| 10,434,142 B2 | 10/2019 | Niazi et al. |
| 10,434,210 B2 | 10/2019 | Olson et al. |
| 10,434,284 B2 | 10/2019 | Hanson et al. |
| 10,449,094 B2 | 10/2019 | Donda et al. |
| D866,756 S | 11/2019 | Allen et al. |
| 10,463,760 B2 | 11/2019 | Karthikeyan et al. |
| 10,463,773 B2 | 11/2019 | Haggstrom et al. |
| 10,470,933 B2 | 11/2019 | Riesinger |
| 10,470,936 B2 | 11/2019 | Wohlgemuth et al. |
| 10,471,122 B2 | 11/2019 | Shi et al. |
| 10,471,190 B2 | 11/2019 | Locke et al. |
| 10,478,345 B2 | 11/2019 | Barta et al. |
| 10,478,346 B2 | 11/2019 | Knutson |
| 10,478,394 B2 | 11/2019 | Yu |
| 10,485,707 B2 | 11/2019 | Sexton |
| 10,485,891 B2 | 11/2019 | Andrews et al. |
| 10,485,892 B2 | 11/2019 | Hands et al. |
| 10,485,906 B2 | 11/2019 | Freedman et al. |
| 10,486,135 B2 | 11/2019 | Yang et al. |
| 10,492,956 B2 | 12/2019 | Zamierowski |
| 10,493,178 B2 | 12/2019 | Marchant et al. |
| 10,493,184 B2 | 12/2019 | Collinson et al. |
| 10,493,185 B2 | 12/2019 | Stokes et al. |
| 10,500,099 B2 | 12/2019 | Hung et al. |
| 10,500,103 B2 | 12/2019 | Croizat et al. |
| 10,500,104 B2 | 12/2019 | Sookraj |
| 10,500,173 B2 | 12/2019 | Yang et al. |
| 10,500,235 B2 | 12/2019 | Wardell |
| 10,500,300 B2 | 12/2019 | Dybe et al. |
| 10,500,301 B2 | 12/2019 | Laurensou |
| 10,500,302 B2 | 12/2019 | Holm et al. |
| 10,501,487 B2 | 12/2019 | Andrews et al. |
| 10,506,928 B2 | 12/2019 | Locke et al. |
| 10,507,141 B2 | 12/2019 | Allen et al. |
| 10,507,259 B2 | 12/2019 | Cree et al. |
| 10,512,707 B2 | 12/2019 | Whalen, III et al. |
| 10,525,170 B2 | 1/2020 | Havenstrite et al. |
| 10,532,137 B2 | 1/2020 | Pratt et al. |
| 10,532,194 B2 | 1/2020 | Locke et al. |
| 10,537,657 B2 | 1/2020 | Phillips et al. |
| 10,542,936 B2 | 1/2020 | Goldberg et al. |
| 10,543,133 B2 | 1/2020 | Shaw et al. |
| 10,543,293 B2 | 1/2020 | Suschek |
| 10,548,777 B2 | 2/2020 | Locke et al. |
| 10,549,008 B2 | 2/2020 | Yoo |
| 10,549,016 B2 | 2/2020 | Bushko et al. |
| 10,549,017 B2 | 2/2020 | Hsiao et al. |
| 10,555,838 B2 | 2/2020 | Wu et al. |
| 10,555,839 B2 | 2/2020 | Hartwell |
| 10,556,044 B2 | 2/2020 | Robinson et al. |
| 10,561,533 B2 | 2/2020 | Hoggarth et al. |
| 10,561,536 B2 | 2/2020 | Holm et al. |
| 10,568,767 B2 | 2/2020 | Addison et al. |
| 10,568,768 B2 | 2/2020 | Long et al. |
| 10,568,770 B2 | 2/2020 | Robinson et al. |
| 10,568,771 B2 | 2/2020 | MacDonald et al. |
| 10,568,773 B2 | 2/2020 | Tuck et al. |
| 10,568,983 B2 | 2/2020 | Gerdes et al. |
| 10,575,991 B2 | 3/2020 | Dunn |
| 10,575,992 B2 | 3/2020 | Sarangapani et al. |
| 10,576,037 B2 | 3/2020 | Harrell |
| 10,576,189 B2 | 3/2020 | Locke et al. |
| 10,583,042 B2 | 3/2020 | Sarangapani et al. |
| 10,583,228 B2 | 3/2020 | Shuler et al. |
| 10,589,007 B2 | 3/2020 | Coulthard et al. |
| 10,590,184 B2 | 3/2020 | Kuo |
| 10,610,414 B2 | 4/2020 | Hartwell et al. |
| 10,610,415 B2 | 4/2020 | Griffey et al. |
| 10,610,623 B2 | 4/2020 | Robinson et al. |

(56) References Cited

U.S. PATENT DOCUMENTS

| | | |
|---|---|---|
| 10,617,569 B2 | 4/2020 | Bonn |
| 10,617,608 B2 | 4/2020 | Shin et al. |
| 10,617,769 B2 | 4/2020 | Huang |
| 10,617,784 B2 | 4/2020 | Yu et al. |
| 10,617,786 B2 | 4/2020 | Kluge et al. |
| 10,618,266 B2 | 4/2020 | Wright et al. |
| 10,624,984 B2 | 4/2020 | Courage et al. |
| 10,625,002 B2 | 4/2020 | Locke et al. |
| 10,632,019 B2 | 4/2020 | Vitaris |
| 10,632,224 B2 | 4/2020 | Hardy et al. |
| 10,639,206 B2 | 5/2020 | Hu et al. |
| 10,639,350 B2 | 5/2020 | Arber et al. |
| 10,639,404 B2 | 5/2020 | Lichtenstein |
| 10,646,614 B2 | 5/2020 | Grinstaff et al. |
| 10,653,562 B2 | 5/2020 | Robinson et al. |
| 10,653,782 B2 | 5/2020 | Ameer et al. |
| 10,653,810 B2 | 5/2020 | Datt et al. |
| 10,653,821 B2 | 5/2020 | Nichols |
| 10,653,823 B2 | 5/2020 | Bharti et al. |
| 10,660,799 B2 | 5/2020 | Wu et al. |
| 10,660,851 B2 | 5/2020 | Millis et al. |
| 10,660,992 B2 | 5/2020 | Canner et al. |
| 10,660,994 B2 | 5/2020 | Askem et al. |
| 10,667,955 B2 | 6/2020 | Allen et al. |
| 10,667,956 B2 | 6/2020 | Van Holten et al. |
| 10,682,257 B2 | 6/2020 | Lu |
| 10,682,258 B2 | 6/2020 | Manwaring et al. |
| 10,682,259 B2 | 6/2020 | Hunt et al. |
| 10,682,318 B2 | 6/2020 | Twomey et al. |
| 10,682,386 B2 | 6/2020 | Ellis-Behnke et al. |
| 10,682,446 B2 | 6/2020 | Askem et al. |
| 10,687,983 B2 | 6/2020 | Dahlberg et al. |
| 10,687,985 B2 | 6/2020 | Lee et al. |
| 10,688,215 B2 | 6/2020 | Munro et al. |
| 10,688,217 B2 | 6/2020 | Hanson et al. |
| RE48,117 E | 7/2020 | Albert et al. |
| 10,702,419 B2 | 7/2020 | Locke et al. |
| 10,702,420 B2 | 7/2020 | Hammond et al. |
| 10,703,942 B2 | 7/2020 | Tunius |
| 10,709,760 B2 | 7/2020 | Gronberg et al. |
| 10,709,807 B2 | 7/2020 | Kshirsagar |
| 10,709,883 B2 | 7/2020 | Spector |
| 10,716,711 B2 | 7/2020 | Locke et al. |
| 10,716,874 B2 | 7/2020 | Koyama et al. |
| 10,729,589 B2 | 8/2020 | Dorian et al. |
| 10,729,590 B2 | 8/2020 | Simmons et al. |
| 10,729,826 B2 | 8/2020 | Lin |
| 10,736,787 B2 | 8/2020 | Hannigan et al. |
| 10,736,788 B2 | 8/2020 | Locke et al. |
| 10,736,985 B2 | 8/2020 | Odermatt et al. |
| 10,737,003 B2 | 8/2020 | Fujisaki |
| 10,743,900 B2 | 8/2020 | Ingram et al. |
| 10,744,040 B2 | 8/2020 | Kazala, Jr. et al. |
| 10,744,041 B2 | 8/2020 | Hartwell |
| 10,744,225 B2 | 8/2020 | Lindgren et al. |
| 10,744,237 B2 | 8/2020 | Guidi et al. |
| 10,744,238 B2 | 8/2020 | Guidi et al. |
| 10,744,239 B2 | 8/2020 | Armstrong et al. |
| 10,744,240 B2 | 8/2020 | Simmons et al. |
| 10,751,212 B2 | 8/2020 | Raza et al. |
| 10,751,442 B2 | 8/2020 | Bonnefin et al. |
| 10,751,452 B2 | 8/2020 | Topaz |
| 10,758,423 B2 | 9/2020 | Pigg et al. |
| 10,758,424 B2 | 9/2020 | Blott et al. |
| 10,758,425 B2 | 9/2020 | Blott et al. |
| 10,758,426 B2 | 9/2020 | Eddy |
| 10,758,651 B2 | 9/2020 | Blott et al. |
| 10,765,561 B2 | 9/2020 | Lattimore et al. |
| 10,765,783 B2 | 9/2020 | Locke et al. |
| 10,772,767 B2 | 9/2020 | Bjork et al. |
| 10,772,999 B2 | 9/2020 | Svensby |
| 10,779,993 B2 | 9/2020 | Bishop et al. |
| 10,780,114 B2 | 9/2020 | Udagawa et al. |
| 10,780,194 B2 | 9/2020 | Flach et al. |
| 10,780,201 B2 | 9/2020 | Lin |
| 10,780,202 B2 | 9/2020 | Askem et al. |
| 10,780,203 B2 | 9/2020 | Coulthard et al. |
| 10,782,238 B2 | 9/2020 | Hicks et al. |
| 10,792,191 B2 | 10/2020 | Robinson et al. |
| 10,792,192 B2 | 10/2020 | Tout et al. |
| 10,792,337 B2 | 10/2020 | Leung et al. |
| 10,792,404 B2 | 10/2020 | Hu et al. |
| 10,792,482 B2 | 10/2020 | Randolph et al. |
| 10,800,905 B2 | 10/2020 | Delli-Santi et al. |
| 10,806,819 B2 | 10/2020 | Shuler |
| 2002/0091074 A1 | 7/2002 | Wooley et al. |
| 2002/0160941 A1 | 10/2002 | Kruzel |
| 2002/0172709 A1 | 11/2002 | Nielsen et al. |
| 2002/0183808 A1 | 12/2002 | Biel |
| 2003/0180345 A1 | 9/2003 | Hill et al. |
| 2003/0180346 A1 | 9/2003 | Woods |
| 2004/0001880 A1 | 1/2004 | Bowler et al. |
| 2004/0247652 A1 | 12/2004 | Sabesan |
| 2005/0059731 A1 | 3/2005 | Albrecht et al. |
| 2006/0019571 A1 | 1/2006 | Lange et al. |
| 2006/0051385 A1 | 3/2006 | Scholz |
| 2006/0051430 A1 | 3/2006 | Arata et al. |
| 2006/0115440 A1 | 6/2006 | Arata et al. |
| 2006/0155260 A1 | 7/2006 | Blott et al. |
| 2006/0172000 A1 | 8/2006 | Cullen et al. |
| 2006/0234959 A1 | 10/2006 | Biel et al. |
| 2006/0254988 A1 | 11/2006 | Frampton |
| 2007/0042024 A1 | 2/2007 | Gladman et al. |
| 2007/0134136 A1 | 6/2007 | Polyakov et al. |
| 2007/0166399 A1 | 7/2007 | Burton et al. |
| 2007/0185426 A1 | 8/2007 | Ambrosio et al. |
| 2007/0219512 A1 | 9/2007 | Heaton et al. |
| 2007/0239078 A1 | 10/2007 | Jaeb |
| 2007/0255192 A1 | 11/2007 | Patel et al. |
| 2008/0112920 A1 | 5/2008 | Chia et al. |
| 2008/0188558 A1 | 8/2008 | Godal et al. |
| 2008/0226724 A1 | 9/2008 | Ji et al. |
| 2009/0012440 A1 | 1/2009 | Bray et al. |
| 2009/0177135 A1 | 7/2009 | Rogers et al. |
| 2009/0234307 A1 | 9/2009 | Vitaris |
| 2009/0259203 A1 | 10/2009 | Hu et al. |
| 2009/0293887 A1 | 12/2009 | Wilkes et al. |
| 2009/0299303 A1 | 12/2009 | Seegert |
| 2010/0015208 A1 | 1/2010 | Kershaw et al. |
| 2010/0030178 A1 | 2/2010 | MacMeccan et al. |
| 2010/0113537 A1 | 5/2010 | Nonaka |
| 2010/0125233 A1 | 5/2010 | Edward S. et al. |
| 2010/0125258 A1 | 5/2010 | Coulthard et al. |
| 2010/0129633 A1 | 5/2010 | Law |
| 2010/0137775 A1 | 6/2010 | Hu et al. |
| 2010/0185163 A1 | 7/2010 | Heagle |
| 2010/0298790 A1 | 11/2010 | Guidi et al. |
| 2010/0310845 A1 | 12/2010 | Bond et al. |
| 2011/0015595 A1 | 1/2011 | Robinson et al. |
| 2011/0028918 A1 | 2/2011 | Hartwell |
| 2011/0112457 A1 | 5/2011 | Holm et al. |
| 2011/0117025 A1 | 5/2011 | Dacosta et al. |
| 2011/0178451 A1 | 7/2011 | Robinson et al. |
| 2011/0224593 A1 | 9/2011 | Tunius |
| 2011/0224630 A1 | 9/2011 | Simmons et al. |
| 2011/0230849 A1 | 9/2011 | Coulthard et al. |
| 2011/0237994 A1 | 9/2011 | Russ et al. |
| 2011/0251566 A1 | 10/2011 | Zimnitsky et al. |
| 2011/0257572 A1 | 10/2011 | Locke et al. |
| 2011/0257573 A1 | 10/2011 | Hong et al. |
| 2011/0275972 A1 | 11/2011 | Rosenberg |
| 2011/0319808 A1 | 12/2011 | Bowler et al. |
| 2012/0071845 A1 | 3/2012 | Hu et al. |
| 2012/0130332 A1 | 5/2012 | Cotton et al. |
| 2012/0136325 A1 | 5/2012 | Allen et al. |
| 2012/0202398 A1 | 8/2012 | Marshall et al. |
| 2012/0209226 A1 | 8/2012 | Simmons et al. |
| 2012/0232502 A1 | 9/2012 | Lowing |
| 2013/0053795 A1 | 2/2013 | Coulthard et al. |
| 2013/0123728 A1 | 5/2013 | Pratt et al. |
| 2013/0226063 A1 | 8/2013 | Taylor et al. |
| 2014/0005618 A1 | 1/2014 | Locke et al. |
| 2014/0074053 A1 | 3/2014 | Locke et al. |
| 2014/0188060 A1 | 7/2014 | Robinson et al. |

(56) References Cited

U.S. PATENT DOCUMENTS

| | | |
|---|---|---|
| 2014/0194838 A1 | 7/2014 | Wibaux et al. |
| 2014/0200532 A1 | 7/2014 | Robinson et al. |
| 2014/0236112 A1 | 8/2014 | Von Wolff et al. |
| 2014/0256925 A1 | 9/2014 | Catchmark et al. |
| 2014/0276499 A1 | 9/2014 | Locke et al. |
| 2014/0296804 A1 | 10/2014 | Hicks et al. |
| 2014/0308338 A1 | 10/2014 | Nierle et al. |
| 2014/0309574 A1 | 10/2014 | Cotton |
| 2015/0018433 A1 | 1/2015 | Leipzig et al. |
| 2015/0057624 A1 | 2/2015 | Simmons et al. |
| 2015/0071985 A1 | 3/2015 | Walker et al. |
| 2015/0079152 A1 | 3/2015 | Wuollett et al. |
| 2015/0094674 A1 | 4/2015 | Pratt et al. |
| 2015/0104486 A1 | 4/2015 | Bonnefin et al. |
| 2015/0112311 A1 | 4/2015 | Hammond et al. |
| 2015/0119831 A1 | 4/2015 | Robinson et al. |
| 2015/0119834 A1 | 4/2015 | Locke et al. |
| 2015/0141941 A1 | 5/2015 | Allen et al. |
| 2015/0148785 A1 | 5/2015 | Kleiner |
| 2015/0174304 A1 | 6/2015 | Askem et al. |
| 2015/0245949 A1 | 9/2015 | Locke et al. |
| 2015/0246164 A1 | 9/2015 | Heaton et al. |
| 2015/0250979 A1 | 9/2015 | Loske |
| 2015/0265741 A1 | 9/2015 | Duncan et al. |
| 2015/0265743 A1 | 9/2015 | Hanson et al. |
| 2015/0320901 A1 | 11/2015 | Chandrashekhar-Bhat et al. |
| 2016/0008293 A1 | 1/2016 | Shi et al. |
| 2016/0038626 A1 | 2/2016 | Locke et al. |
| 2016/0051724 A1 | 2/2016 | Sahin et al. |
| 2016/0067107 A1 | 3/2016 | Cotton |
| 2016/0100987 A1 | 4/2016 | Hartwell et al. |
| 2016/0101207 A1 | 4/2016 | Parsons et al. |
| 2016/0106878 A1 | 4/2016 | Yang et al. |
| 2016/0106892 A1 | 4/2016 | Hartwell |
| 2016/0166422 A1 | 6/2016 | Karim et al. |
| 2016/0193244 A1 | 7/2016 | Ota et al. |
| 2016/0222548 A1 | 8/2016 | Agboh |
| 2016/0271178 A1 | 9/2016 | Hauser et al. |
| 2016/0287743 A1 | 10/2016 | Andrews |
| 2016/0339158 A1 | 11/2016 | Collinson et al. |
| 2016/0374847 A1 | 12/2016 | Lachenbruch et al. |
| 2017/0014275 A1 | 1/2017 | Schneider |
| 2017/0049111 A1 | 2/2017 | Patton et al. |
| 2017/0072669 A1 | 3/2017 | Sekido et al. |
| 2017/0079276 A1 | 3/2017 | Percival et al. |
| 2017/0128269 A1 | 5/2017 | Coulthard et al. |
| 2017/0189237 A1 | 7/2017 | Locke et al. |
| 2017/0189575 A1 | 7/2017 | Lee et al. |
| 2017/0209615 A1 | 7/2017 | Tornero Garcia et al. |
| 2017/0232161 A1 | 8/2017 | Fewkes et al. |
| 2017/0258956 A1 | 9/2017 | Flach et al. |
| 2017/0347661 A1 | 12/2017 | Parsons |
| 2017/0367895 A1 | 12/2017 | Holm et al. |
| 2017/0368239 A1 | 12/2017 | Askem et al. |
| 2018/0008742 A1 | 1/2018 | Hoggarth et al. |
| 2018/0014974 A1 | 1/2018 | Hoggarth et al. |
| 2018/0023217 A1 | 1/2018 | Patton et al. |
| 2018/0030321 A1 | 2/2018 | Tunius |
| 2018/0042789 A1 | 2/2018 | Bradford et al. |
| 2018/0078423 A1 | 3/2018 | Magin et al. |
| 2018/0086903 A1 | 3/2018 | Zhang et al. |
| 2018/0118809 A1 | 5/2018 | Mearns Spragg |
| 2018/0133066 A1 | 5/2018 | Ahsani et al. |
| 2018/0140467 A1 | 5/2018 | Hunt |
| 2018/0140822 A1 | 5/2018 | Robinson et al. |
| 2018/0200414 A1 | 7/2018 | Askem et al. |
| 2018/0221531 A1 | 8/2018 | Bender et al. |
| 2018/0236124 A1 | 8/2018 | Young et al. |
| 2018/0243463 A1 | 8/2018 | Chatterjee et al. |
| 2018/0243464 A1 | 8/2018 | Hwang et al. |
| 2018/0244857 A1 | 8/2018 | Lee et al. |
| 2018/0272052 A1 | 9/2018 | Locke et al. |
| 2018/0296397 A1 | 10/2018 | Askem et al. |
| 2018/0303873 A1 | 10/2018 | Been et al. |
| 2018/0311419 A1 | 11/2018 | Locke et al. |
| 2018/0333522 A1 | 11/2018 | Pratt et al. |
| 2018/0344533 A1 | 12/2018 | Rovaniemi |
| 2018/0353334 A1 | 12/2018 | Locke et al. |
| 2018/0353337 A1 | 12/2018 | Locke |
| 2018/0353339 A1 | 12/2018 | Locke et al. |
| 2018/0353340 A1 | 12/2018 | Robinson et al. |
| 2018/0353344 A1 | 12/2018 | Locke et al. |
| 2018/0353662 A1 | 12/2018 | Locke et al. |
| 2018/0353663 A1 | 12/2018 | Locke et al. |
| 2018/0360667 A1 | 12/2018 | Droche |
| 2019/0000677 A1 | 1/2019 | Munro |
| 2019/0015258 A1 | 1/2019 | Gowans et al. |
| 2019/0015468 A1 | 1/2019 | Yadav et al. |
| 2019/0030223 A1 | 1/2019 | Lin |
| 2019/0046682 A1 | 2/2019 | Choi et al. |
| 2019/0060127 A1 | 2/2019 | Locke et al. |
| 2019/0083752 A1 | 3/2019 | Howell et al. |
| 2019/0117465 A1 | 4/2019 | Osborne et al. |
| 2019/0117466 A1 | 4/2019 | Kazala, Jr. et al. |
| 2019/0117861 A1 | 4/2019 | Locke et al. |
| 2019/0125590 A1 | 5/2019 | Rehbein et al. |
| 2019/0133830 A1 | 5/2019 | Bishop et al. |
| 2019/0151155 A1 | 5/2019 | Bonn |
| 2019/0151159 A1 | 5/2019 | Gowans et al. |
| 2019/0151495 A1 | 5/2019 | Helary et al. |
| 2019/0184052 A1 | 6/2019 | Ilan et al. |
| 2019/0231600 A1 | 8/2019 | Locke et al. |
| 2019/0231602 A1 | 8/2019 | Locke et al. |
| 2019/0231943 A1 | 8/2019 | Robinson et al. |
| 2019/0274889 A1 | 9/2019 | Steward et al. |
| 2019/0282728 A1 | 9/2019 | Kellar et al. |
| 2019/0290799 A1 | 9/2019 | Arshi et al. |
| 2019/0298249 A1 | 10/2019 | Bates et al. |
| 2019/0298577 A1 | 10/2019 | Locke et al. |
| 2019/0298578 A1 | 10/2019 | Shulman et al. |
| 2019/0298579 A1 | 10/2019 | Moore et al. |
| 2019/0298580 A1 | 10/2019 | Hall et al. |
| 2019/0298582 A1 | 10/2019 | Addison et al. |
| 2019/0298881 A1 | 10/2019 | Ramjit et al. |
| 2019/0298882 A1 | 10/2019 | Nelson |
| 2019/0298895 A1 | 10/2019 | Selby et al. |
| 2019/0307611 A1 | 10/2019 | Askem et al. |
| 2019/0307612 A1 | 10/2019 | Hartwell et al. |
| 2019/0307934 A1 | 10/2019 | Allen et al. |
| 2019/0307935 A1 | 10/2019 | Simmons et al. |
| 2019/0314187 A1 | 10/2019 | Emslander et al. |
| 2019/0314209 A1 | 10/2019 | Ha et al. |
| 2019/0314544 A1 | 10/2019 | Filho et al. |
| 2019/0321232 A1 | 10/2019 | Jardret et al. |
| 2019/0321509 A1 | 10/2019 | Chakravarthy et al. |
| 2019/0321526 A1 | 10/2019 | Robinson et al. |
| 2019/0322795 A1 | 10/2019 | Kubo et al. |
| 2019/0328580 A1 | 10/2019 | Emslander et al. |
| 2019/0336343 A1 | 11/2019 | Etchells et al. |
| 2019/0336344 A1 | 11/2019 | Locke |
| 2019/0336345 A1 | 11/2019 | Bannwart |
| 2019/0336346 A1 | 11/2019 | Locke et al. |
| 2019/0336640 A1 | 11/2019 | Vismara et al. |
| 2019/0336641 A1 | 11/2019 | Nisbet |
| 2019/0336643 A1 | 11/2019 | Luukko et al. |
| 2019/0336658 A1 | 11/2019 | Heaton et al. |
| 2019/0336739 A1 | 11/2019 | Locke et al. |
| 2019/0343687 A1 | 11/2019 | Locke et al. |
| 2019/0343889 A1 | 11/2019 | Luukko et al. |
| 2019/0343979 A1 | 11/2019 | Kearney et al. |
| 2019/0343993 A1 | 11/2019 | Weston |
| 2019/0343994 A1 | 11/2019 | Greener |
| 2019/0344242 A1 | 11/2019 | Kim et al. |
| 2019/0350763 A1 | 11/2019 | Pratt et al. |
| 2019/0350764 A1 | 11/2019 | Zochowski et al. |
| 2019/0350765 A1 | 11/2019 | Heagle et al. |
| 2019/0350775 A1 | 11/2019 | Biasutti et al. |
| 2019/0350970 A1 | 11/2019 | Saphier et al. |
| 2019/0351092 A1 | 11/2019 | Silver et al. |
| 2019/0351093 A1 | 11/2019 | Stein et al. |
| 2019/0351094 A1 | 11/2019 | Maher et al. |
| 2019/0351095 A1 | 11/2019 | Maher et al. |
| 2019/0351111 A1 | 11/2019 | Locke et al. |
| 2019/0358088 A1 | 11/2019 | Lavocah et al. |

(56) References Cited

U.S. PATENT DOCUMENTS

| | | |
|---|---|---|
| 2019/0358361 A1 | 11/2019 | Mcinnes et al. |
| 2019/0358372 A1 | 11/2019 | Askem et al. |
| 2019/0365948 A1 | 12/2019 | Deegan et al. |
| 2019/0365962 A1 | 12/2019 | Lee et al. |
| 2019/0374408 A1 | 12/2019 | Robles et al. |
| 2019/0374673 A1 | 12/2019 | Hoefinghoff et al. |
| 2019/0380878 A1 | 12/2019 | Edwards et al. |
| 2019/0380881 A1 | 12/2019 | Albert et al. |
| 2019/0380882 A1 | 12/2019 | Taylor et al. |
| 2019/0380883 A1 | 12/2019 | Macphee et al. |
| 2019/0381222 A9 | 12/2019 | Locke et al. |
| 2019/0388577 A1 | 12/2019 | Chandrashekhar-Bhat et al. |
| 2019/0388579 A1 | 12/2019 | Macphee et al. |
| 2019/0388589 A1 | 12/2019 | Macphee et al. |
| 2020/0000640 A1 | 1/2020 | Mondal et al. |
| 2020/0000642 A1 | 1/2020 | Waite |
| 2020/0000643 A1 | 1/2020 | Locke |
| 2020/0000955 A1 | 1/2020 | Andrews et al. |
| 2020/0000956 A1 | 1/2020 | Huang et al. |
| 2020/0000960 A1 | 1/2020 | Kellar et al. |
| 2020/0000985 A1 | 1/2020 | Seddon et al. |
| 2020/0008981 A1 | 1/2020 | Wheldrake |
| 2020/0009289 A1 | 1/2020 | Torabinejad et al. |
| 2020/0009400 A1 | 1/2020 | Ribeiro et al. |
| 2020/0017650 A1 | 1/2020 | Young et al. |
| 2020/0022844 A1 | 1/2020 | Blott et al. |
| 2020/0023102 A1 | 1/2020 | Powell |
| 2020/0023103 A1 | 1/2020 | Joshi et al. |
| 2020/0023104 A1 | 1/2020 | Eriksson et al. |
| 2020/0023105 A1 | 1/2020 | Long et al. |
| 2020/0023106 A1 | 1/2020 | Carroll et al. |
| 2020/0030153 A1 | 1/2020 | Johannison et al. |
| 2020/0030480 A1 | 1/2020 | Choi |
| 2020/0030499 A1 | 1/2020 | Menon et al. |
| 2020/0038023 A1 | 2/2020 | Dunn |
| 2020/0038249 A1 | 2/2020 | Pratt et al. |
| 2020/0038250 A1 | 2/2020 | Edwards et al. |
| 2020/0038251 A1 | 2/2020 | Locke et al. |
| 2020/0038252 A1 | 2/2020 | Spiro |
| 2020/0038283 A1 | 2/2020 | Hall et al. |
| 2020/0038470 A1 | 2/2020 | Datt et al. |
| 2020/0038544 A1 | 2/2020 | Grover et al. |
| 2020/0038546 A1 | 2/2020 | Dizio et al. |
| 2020/0038639 A1 | 2/2020 | Patel et al. |
| 2020/0046565 A1 | 2/2020 | Barta et al. |
| 2020/0046566 A1 | 2/2020 | Carey et al. |
| 2020/0046567 A1 | 2/2020 | Carroll et al. |
| 2020/0046568 A1 | 2/2020 | Sexton |
| 2020/0046663 A1 | 2/2020 | Murdock et al. |
| 2020/0046876 A1 | 2/2020 | Liu |
| 2020/0046887 A1 | 2/2020 | Runquist et al. |
| 2020/0054491 A1 | 2/2020 | Hentrich et al. |
| 2020/0054781 A1 | 2/2020 | Weiser et al. |
| 2020/0060879 A1 | 2/2020 | Edwards et al. |
| 2020/0061253 A1 | 2/2020 | Long et al. |
| 2020/0061254 A1 | 2/2020 | Joshi et al. |
| 2020/0061379 A1 | 2/2020 | Bogie et al. |
| 2020/0069183 A1 | 3/2020 | Rice et al. |
| 2020/0069476 A1 | 3/2020 | Randolph et al. |
| 2020/0069477 A1 | 3/2020 | Holm et al. |
| 2020/0069478 A1 | 3/2020 | Jabbarzadeh et al. |
| 2020/0069479 A1 | 3/2020 | Buan et al. |
| 2020/0069835 A1 | 3/2020 | Hissink et al. |
| 2020/0069850 A1 | 3/2020 | Beadle et al. |
| 2020/0069851 A1 | 3/2020 | Blott et al. |
| 2020/0069853 A1 | 3/2020 | Hall et al. |
| 2020/0078223 A1 | 3/2020 | Locke et al. |
| 2020/0078224 A1 | 3/2020 | Carroll et al. |
| 2020/0078225 A1 | 3/2020 | Grillitsch et al. |
| 2020/0078305 A1 | 3/2020 | Auvinen et al. |
| 2020/0078330 A1 | 3/2020 | Gay |
| 2020/0078482 A1 | 3/2020 | Yoon et al. |
| 2020/0078499 A1 | 3/2020 | Gadde et al. |
| 2020/0085625 A1 | 3/2020 | Bellini et al. |
| 2020/0085626 A1 | 3/2020 | Braga et al. |
| 2020/0085629 A1 | 3/2020 | Locke et al. |
| 2020/0085630 A1 | 3/2020 | Robinson et al. |
| 2020/0085632 A1 | 3/2020 | Locke et al. |
| 2020/0085991 A1 | 3/2020 | Coomber |
| 2020/0085992 A1 | 3/2020 | Locke et al. |
| 2020/0086014 A1 | 3/2020 | Locke et al. |
| 2020/0086017 A1 | 3/2020 | Jardret et al. |
| 2020/0086049 A1 | 3/2020 | Park et al. |
| 2020/0093646 A1 | 3/2020 | Locke et al. |
| 2020/0093756 A1 | 3/2020 | Sabacinski |
| 2020/0093953 A1 | 3/2020 | Kim et al. |
| 2020/0093954 A1 | 3/2020 | Leise, III |
| 2020/0093970 A1 | 3/2020 | Hunt et al. |
| 2020/0095421 A1 | 3/2020 | Kettel |
| 2020/0100945 A1 | 4/2020 | Albert et al. |
| 2020/0101192 A1 | 4/2020 | Folwarzny |
| 2020/0107964 A1 | 4/2020 | Locke et al. |
| 2020/0107965 A1 | 4/2020 | Greener |
| 2020/0107966 A1 | 4/2020 | Francis |
| 2020/0107967 A1 | 4/2020 | Holm et al. |
| 2020/0108169 A1 | 4/2020 | Hu et al. |
| 2020/0113741 A1 | 4/2020 | Rehbein et al. |
| 2020/0114039 A1 | 4/2020 | Wang et al. |
| 2020/0114040 A1 | 4/2020 | Waite et al. |
| 2020/0114049 A1 | 4/2020 | Wall |
| 2020/0121509 A1 | 4/2020 | Locke et al. |
| 2020/0121510 A1 | 4/2020 | Hartwell et al. |
| 2020/0121513 A1 | 4/2020 | Townsend et al. |
| 2020/0121521 A1 | 4/2020 | Daniel et al. |
| 2020/0121833 A9 | 4/2020 | Askem et al. |
| 2020/0129338 A1 | 4/2020 | Gardiner et al. |
| 2020/0129341 A1 | 4/2020 | Coulthard et al. |
| 2020/0129648 A1 | 4/2020 | Drury et al. |
| 2020/0129654 A1 | 4/2020 | Bouvier et al. |
| 2020/0129655 A1 | 4/2020 | Gardiner et al. |
| 2020/0129675 A1 | 4/2020 | Robinson et al. |
| 2020/0138754 A1 | 5/2020 | Johnson |
| 2020/0139002 A1 | 5/2020 | Dudnyk et al. |
| 2020/0139023 A1 | 5/2020 | Haggstrom et al. |
| 2020/0139025 A1 | 5/2020 | Robinson et al. |
| 2020/0141031 A1 | 5/2020 | Kosan et al. |
| 2020/0146894 A1 | 5/2020 | Long et al. |
| 2020/0146896 A1 | 5/2020 | Rice et al. |
| 2020/0146897 A1 | 5/2020 | Locke et al. |
| 2020/0146899 A1 | 5/2020 | Pratt et al. |
| 2020/0155355 A1 | 5/2020 | Hill et al. |
| 2020/0155358 A1 | 5/2020 | Wheldrake |
| 2020/0155359 A1 | 5/2020 | Carroll et al. |
| 2020/0155361 A1 | 5/2020 | Pigg et al. |
| 2020/0155379 A1 | 5/2020 | Shaw et al. |
| 2020/0163802 A1 | 5/2020 | Hunt et al. |
| 2020/0163803 A1 | 5/2020 | Pigg et al. |
| 2020/0164112 A1 | 5/2020 | Kato et al. |
| 2020/0164120 A1 | 5/2020 | Jaecklein et al. |
| 2020/0170841 A1 | 6/2020 | Waite et al. |
| 2020/0170842 A1 | 6/2020 | Locke |
| 2020/0170843 A1 | 6/2020 | Collinson et al. |
| 2020/0171197 A1 | 6/2020 | Hubbell et al. |
| 2020/0179300 A1 | 6/2020 | Urban et al. |
| 2020/0179558 A1 | 6/2020 | Munro et al. |
| 2020/0179673 A1 | 6/2020 | Wan |
| 2020/0188179 A1 | 6/2020 | Bugedo-Albizuri et al. |
| 2020/0188180 A1 | 6/2020 | Akbari et al. |
| 2020/0188182 A1 | 6/2020 | Sanders et al. |
| 2020/0188183 A1 | 6/2020 | Hamerslagh et al. |
| 2020/0188550 A1 | 6/2020 | Dagger et al. |
| 2020/0188564 A1 | 6/2020 | Dunn |
| 2020/0190310 A1 | 6/2020 | Meyer |
| 2020/0197227 A1 | 6/2020 | Locke et al. |
| 2020/0197228 A1 | 6/2020 | Hartwell |
| 2020/0197559 A1 | 6/2020 | Bourdillon et al. |
| 2020/0197580 A1 | 6/2020 | Kilpadi et al. |
| 2020/0206035 A1 | 7/2020 | Kantor et al. |
| 2020/0206036 A1 | 7/2020 | Robinson et al. |
| 2020/0214637 A1 | 7/2020 | Brownhill et al. |
| 2020/0214897 A1 | 7/2020 | Long et al. |
| 2020/0214898 A1 | 7/2020 | Waite et al. |
| 2020/0214899 A1 | 7/2020 | Locke et al. |
| 2020/0215220 A1 | 7/2020 | Schomburg et al. |

(56) References Cited

U.S. PATENT DOCUMENTS

| | | |
|---|---|---|
| 2020/0215226 A1 | 7/2020 | Kitagawa et al. |
| 2020/0222469 A1 | 7/2020 | Cotton |
| 2020/0229983 A1 | 7/2020 | Robinson et al. |
| 2020/0230283 A1 | 7/2020 | Yang et al. |
| 2020/0237562 A1 | 7/2020 | Rice et al. |
| 2020/0237564 A1 | 7/2020 | Hammond et al. |
| 2020/0237816 A1 | 7/2020 | Lait |
| 2020/0246190 A1 | 8/2020 | Luckemeyer et al. |
| 2020/0246191 A1 | 8/2020 | Lu et al. |
| 2020/0246194 A1 | 8/2020 | Gonzalez et al. |
| 2020/0246195 A1 | 8/2020 | Robinson et al. |
| 2020/0253785 A1 | 8/2020 | Bernet et al. |
| 2020/0253786 A1 | 8/2020 | Harrison et al. |
| 2020/0253788 A1 | 8/2020 | Rehbein et al. |
| 2020/0254139 A1 | 8/2020 | Phillips et al. |
| 2020/0261275 A1 | 8/2020 | Manwaring et al. |
| 2020/0261276 A1 | 8/2020 | Lujan Hernandez et al. |
| 2020/0268560 A1 | 8/2020 | Harrison et al. |
| 2020/0268561 A1 | 8/2020 | Locke et al. |
| 2020/0269028 A1 | 8/2020 | Hegg |
| 2020/0270484 A1 | 8/2020 | Lipscomb et al. |
| 2020/0276055 A1 | 9/2020 | Randolph et al. |
| 2020/0276058 A1 | 9/2020 | Locke et al. |
| 2020/0277450 A1 | 9/2020 | Silverstein et al. |
| 2020/0281519 A1 | 9/2020 | Gowans et al. |
| 2020/0281529 A1 | 9/2020 | Grubb et al. |
| 2020/0281678 A1 | 9/2020 | Long et al. |
| 2020/0281775 A1 | 9/2020 | Kushnir et al. |
| 2020/0282100 A1 | 9/2020 | Gil et al. |
| 2020/0282114 A1 | 9/2020 | Long et al. |
| 2020/0282115 A1 | 9/2020 | Gardner et al. |
| 2020/0289326 A1 | 9/2020 | Nielsen et al. |
| 2020/0289327 A1 | 9/2020 | Hansen et al. |
| 2020/0289328 A1 | 9/2020 | Luckemeyer et al. |
| 2020/0289346 A1 | 9/2020 | Hansen et al. |
| 2020/0289347 A1 | 9/2020 | Gowans et al. |
| 2020/0289701 A1 | 9/2020 | Hall et al. |
| 2020/0289712 A1 | 9/2020 | Jiang et al. |
| 2020/0289723 A1 | 9/2020 | Gregory et al. |
| 2020/0289726 A1 | 9/2020 | Locke et al. |
| 2020/0289727 A1 | 9/2020 | Locke |
| 2020/0289806 A1 | 9/2020 | Locke et al. |
| 2020/0297541 A1 | 9/2020 | Hartwell et al. |
| 2020/0297543 A1 | 9/2020 | Rodzewicz et al. |
| 2020/0297544 A1 | 9/2020 | Moine et al. |
| 2020/0297892 A1 | 9/2020 | Silcock |
| 2020/0297893 A1 | 9/2020 | Ericson |
| 2020/0297894 A1 | 9/2020 | Koyama et al. |
| 2020/0299865 A1 | 9/2020 | Bonnefin et al. |
| 2020/0306089 A1 | 10/2020 | Delury et al. |
| 2020/0306091 A1 | 10/2020 | Lee et al. |
| 2020/0306092 A1 | 10/2020 | Rehbein et al. |
| 2020/0306094 A1 | 10/2020 | Kushnir et al. |
| 2020/0306426 A1 | 10/2020 | Rice et al. |
| 2020/0306428 A1 | 10/2020 | Ingram et al. |
| 2020/0306430 A1 | 10/2020 | Rehbein et al. |
| 2020/0315853 A1 | 10/2020 | Waite |
| 2020/0315854 A1 | 10/2020 | Simmons et al. |
| 2020/0315894 A1 | 10/2020 | Churilla et al. |
| 2020/0316271 A1 | 10/2020 | Lin |
| 2020/0316272 A1 | 10/2020 | Simpson |
| 2020/0316273 A1 | 10/2020 | Hegg |
| 2020/0323692 A1 | 10/2020 | Locke et al. |
| 2020/0324015 A1 | 10/2020 | Kettel et al. |
| 2020/0330283 A1 | 10/2020 | Locke et al. |
| 2020/0330284 A1 | 10/2020 | Locke et al. |
| 2020/0330285 A1 | 10/2020 | Rehbein et al. |
| 2020/0330658 A1 | 10/2020 | Fujisaki |
| 2020/0330660 A1 | 10/2020 | Patel et al. |
| 2020/0337719 A1 | 10/2020 | Ingram et al. |
| 2020/0337904 A1 | 10/2020 | Waite |
| 2020/0337905 A1 | 10/2020 | Earl et al. |
| 2020/0337906 A1 | 10/2020 | Long et al. |
| 2020/0337908 A1 | 10/2020 | Long et al. |
| 2020/0338228 A1 | 10/2020 | Kharkar et al. |
| 2020/0338243 A1 | 10/2020 | Harrison et al. |

FOREIGN PATENT DOCUMENTS

| | | |
|---|---|---|
| CN | 101331263 A | 12/2008 |
| CN | 105407930 A | 3/2016 |
| DE | 4001690 A | 8/1990 |
| EP | 0616650 A1 | 9/1994 |
| EP | 0680344 A1 | 11/1995 |
| EP | 1129730 A1 | 9/2001 |
| EP | 1158859 A1 | 12/2001 |
| EP | 1318842 A1 | 6/2003 |
| EP | 1343510 A1 | 9/2003 |
| EP | 1425050 A1 | 6/2004 |
| EP | 1557088 A1 | 7/2005 |
| EP | 1882482 A2 | 1/2008 |
| EP | 1925719 A1 | 5/2008 |
| EP | 1925917 A1 | 5/2008 |
| EP | 1343510 B1 | 5/2010 |
| EP | 2262545 A2 | 12/2010 |
| EP | 2935688 A2 | 10/2015 |
| EP | 2996730 A1 | 3/2016 |
| EP | 3187204 A1 | 7/2017 |
| EP | 3241439 A1 | 11/2017 |
| EP | 3556407 A1 | 10/2019 |
| EP | 3569260 A1 | 11/2019 |
| EP | 3643328 A1 | 4/2020 |
| EP | 3643330 A1 | 4/2020 |
| EP | 3643331 A1 | 4/2020 |
| EP | 3669838 A1 | 6/2020 |
| EP | 3669843 A1 | 6/2020 |
| EP | 3669844 A1 | 6/2020 |
| FR | 2604900 A1 | 4/1988 |
| GB | 735462 A | 8/1955 |
| GB | 1105829 A | 3/1968 |
| GB | 2094802 B | 2/1985 |
| GB | 2220881 B | 7/1992 |
| GB | 2579211 A | 6/2020 |
| GB | 2579368 A | 6/2020 |
| JP | S5138427 A | 3/1976 |
| JP | H07502081 A | 3/1995 |
| JP | H08505790 A | 6/1996 |
| JP | 2000201976 A | 7/2000 |
| JP | 2000510539 A | 8/2000 |
| JP | 2002539140 A | 11/2002 |
| JP | 2003052725 A | 2/2003 |
| JP | 2003510475 A | 3/2003 |
| JP | 2003512095 A | 4/2003 |
| JP | 2003531828 A | 10/2003 |
| JP | 2007509034 A | 4/2007 |
| JP | 2007167266 A | 7/2007 |
| JP | 2007532606 A | 11/2007 |
| JP | 2008502735 A | 1/2008 |
| JP | 2008038293 A | 2/2008 |
| JP | 2008503557 A | 2/2008 |
| JP | 2008507327 A | 3/2008 |
| JP | 2008526997 A | 7/2008 |
| JP | 2009519312 A | 5/2009 |
| JP | 2016040294 A | 3/2016 |
| JP | 2016519966 A | 7/2016 |
| RU | 2092180 C1 | 10/1997 |
| WO | 9218098 A1 | 10/1992 |
| WO | 9312275 A1 | 6/1993 |
| WO | 9319152 A1 | 9/1993 |
| WO | 9402022 A1 | 2/1994 |
| WO | 8401721 A1 | 5/1994 |
| WO | 9416746 A1 | 8/1994 |
| WO | 9601119 A1 | 1/1996 |
| WO | 9702313 A1 | 1/1997 |
| WO | 9606260 A1 | 2/1998 |
| WO | 9846818 A1 | 10/1998 |
| WO | 0054593 A1 | 9/2000 |
| WO | 0072874 A1 | 12/2000 |
| WO | 0123653 A1 | 4/2001 |
| WO | 0124839 A1 | 4/2001 |
| WO | 0128338 A2 | 4/2001 |
| WO | 0128600 A1 | 4/2001 |

(56) References Cited

FOREIGN PATENT DOCUMENTS

| | | |
|---|---|---|
| WO | 0137936 A1 | 5/2001 |
| WO | 0159421 A2 | 8/2001 |
| WO | 0162289 A2 | 8/2001 |
| WO | 0243743 A1 | 6/2002 |
| WO | 02055060 A2 | 7/2002 |
| WO | 02078755 A2 | 10/2002 |
| WO | 03022317 A1 | 3/2003 |
| WO | 03047341 A2 | 6/2003 |
| WO | 03068247 A1 | 8/2003 |
| WO | 2004028461 A2 | 4/2004 |
| WO | 2004035718 A2 | 4/2004 |
| WO | 2004056346 A1 | 7/2004 |
| WO | 2004108093 A2 | 12/2004 |
| WO | 2005018543 A2 | 3/2005 |
| WO | 2005020915 A2 | 3/2005 |
| WO | 2005032459 A2 | 4/2005 |
| WO | 2005079582 A1 | 9/2005 |
| WO | 2005099757 A1 | 10/2005 |
| WO | 2005123103 A1 | 12/2005 |
| WO | 2006000765 A1 | 1/2006 |
| WO | 2006015317 A2 | 2/2006 |
| WO | 2006022970 A1 | 3/2006 |
| WO | 2006029213 A2 | 3/2006 |
| WO | 2006111624 A2 | 10/2006 |
| WO | 2007005720 A2 | 1/2007 |
| WO | 2007068938 A2 | 6/2007 |
| WO | 2008035734 A1 | 3/2008 |
| WO | 2009130608 A2 | 10/2009 |
| WO | 2010070292 A1 | 6/2010 |
| WO | 2011121394 A1 | 10/2011 |
| WO | 2011135284 A1 | 11/2011 |
| WO | 2011144888 A1 | 11/2011 |
| WO | 2012061225 A2 | 5/2012 |
| WO | 2012072980 A1 | 6/2012 |
| WO | 2012136968 A1 | 10/2012 |
| WO | 2013015827 A2 | 1/2013 |
| WO | 2013126049 A1 | 8/2013 |
| WO | 2014014842 A1 | 1/2014 |
| WO | 2014096843 A2 | 6/2014 |
| WO | 2014186590 A1 | 11/2014 |
| WO | 2015145117 A1 | 10/2015 |
| WO | 2015173546 A1 | 11/2015 |
| WO | 2016141450 A1 | 9/2016 |
| WO | 2017016974 A1 | 2/2017 |
| WO | 2017125250 A1 | 7/2017 |
| WO | 2018029231 A1 | 2/2018 |
| WO | 2018094061 A1 | 5/2018 |
| WO | 2018162613 A1 | 9/2018 |
| WO | 2018163093 A1 | 9/2018 |
| WO | 2018189265 A1 | 10/2018 |
| WO | 2018226667 A1 | 12/2018 |
| WO | 2018227144 A1 | 12/2018 |
| WO | 2018231825 A1 | 12/2018 |
| WO | 2018236648 A1 | 12/2018 |
| WO | 2019002085 A1 | 1/2019 |
| WO | 2019012068 A1 | 1/2019 |
| WO | 2019012069 A1 | 1/2019 |
| WO | 2019022493 A1 | 1/2019 |
| WO | 2019027933 A1 | 2/2019 |
| WO | 2019038548 A1 | 2/2019 |
| WO | 2019038549 A1 | 2/2019 |
| WO | 2019040656 A1 | 2/2019 |
| WO | 2019050855 A1 | 3/2019 |
| WO | 2019058373 A1 | 3/2019 |
| WO | 2019073326 A1 | 4/2019 |
| WO | 2019083563 A1 | 5/2019 |
| WO | 2019083868 A1 | 5/2019 |
| WO | 2019086911 A1 | 5/2019 |
| WO | 2019091150 A1 | 5/2019 |
| WO | 2019094147 A1 | 5/2019 |
| WO | 2019096828 A1 | 5/2019 |
| WO | 2019113275 A1 | 6/2019 |
| WO | 2019113623 A1 | 6/2019 |
| WO | 2019191590 A1 | 10/2019 |
| WO | 2019193141 A1 | 10/2019 |
| WO | 2019193333 A1 | 10/2019 |
| WO | 2019199389 A1 | 10/2019 |
| WO | 2019199596 A1 | 10/2019 |
| WO | 2019199687 A1 | 10/2019 |
| WO | 2019199798 A1 | 10/2019 |
| WO | 2019199849 A1 | 10/2019 |
| WO | 2019200035 A1 | 10/2019 |
| WO | 2019215572 A1 | 11/2019 |
| WO | 2019219613 A1 | 11/2019 |
| WO | 2019234365 A1 | 12/2019 |
| WO | 2020005062 A1 | 1/2020 |
| WO | 2020005344 A1 | 1/2020 |
| WO | 2020005536 A1 | 1/2020 |
| WO | 2020005546 A1 | 1/2020 |
| WO | 2020005577 A1 | 1/2020 |
| WO | 2020007429 A1 | 1/2020 |
| WO | 2020011691 A1 | 1/2020 |
| WO | 2020014178 A1 | 1/2020 |
| WO | 2020014310 A1 | 1/2020 |
| WO | 2020018300 A1 | 1/2020 |
| WO | 2020026061 A1 | 2/2020 |
| WO | 2020026144 A1 | 2/2020 |
| WO | 2020033351 A1 | 2/2020 |
| WO | 2020035811 A1 | 2/2020 |
| WO | 2020043665 A1 | 3/2020 |
| WO | 2020044237 A1 | 3/2020 |
| WO | 2020046443 A1 | 3/2020 |
| WO | 2020047255 A1 | 3/2020 |
| WO | 2020049038 A1 | 3/2020 |
| WO | 2020055945 A1 | 3/2020 |
| WO | 2020056014 A1 | 3/2020 |
| WO | 2020056182 A1 | 3/2020 |
| WO | 2020065531 A1 | 4/2020 |
| WO | 2020070231 A1 | 4/2020 |
| WO | 2020074512 A1 | 4/2020 |
| WO | 2020078993 A1 | 4/2020 |
| WO | 2020079009 A1 | 4/2020 |
| WO | 2020079330 A1 | 4/2020 |
| WO | 2020081259 A1 | 4/2020 |
| WO | 2020081391 A1 | 4/2020 |
| WO | 2020092598 A1 | 5/2020 |
| WO | 2020136555 A1 | 7/2020 |
| WO | 2020141059 A1 | 7/2020 |
| WO | 2020144347 A1 | 7/2020 |
| WO | 2020150548 A1 | 7/2020 |
| WO | 2020159675 A1 | 8/2020 |
| WO | 2020159677 A1 | 8/2020 |
| WO | 2020159678 A1 | 8/2020 |
| WO | 2020159823 A1 | 8/2020 |
| WO | 2020159859 A1 | 8/2020 |
| WO | 2020159892 A1 | 8/2020 |
| WO | 2020161086 A1 | 8/2020 |
| WO | 2020173665 A1 | 9/2020 |
| WO | 2020173760 A1 | 9/2020 |
| WO | 2020174264 A1 | 9/2020 |
| WO | 2020174510 A1 | 9/2020 |
| WO | 2020182887 A1 | 9/2020 |
| WO | 2020185810 A1 | 9/2020 |
| WO | 2020197759 A1 | 10/2020 |
| WO | 2020197760 A1 | 10/2020 |
| WO | 2020198484 A1 | 10/2020 |
| WO | 2020201879 A1 | 10/2020 |
| WO | 2020213998 A1 | 10/2020 |

OTHER PUBLICATIONS

India Patent Application No. 9392/DELNP/2013 First Examination Report dated Feb. 23, 2018.
International Wound Infection Institute (IWII). Wound infection in clinical practice. Wounds International, 2016. http://www.woundinfection-institute.com/wp-content/uploads/2017/03/IWII-Wound-infection-in-clinical-practice.pdf. Accessed Jul. 2, 2018.
James G, Swogger E, Wolcott R et al. Biofilms in chronic wounds. Wound Repair Regen. 2008; 16: 37-44.
Japanese Patent Application No. 2017-112806 Official Action dated Mar. 6, 2018.
Japanese Patent Application No. 2013-541415 Final Rejection dated Jun. 14, 2016.

(56) References Cited

OTHER PUBLICATIONS

Japanese Patent Application No. 2014-242257 Office Action dated Apr. 5, 2016.
Japanese Patent Application No. 2014-242257 Office Action dated May 23, 2017.
Japanese Patent Application No. 2014-543972 Office Action dated Dec. 20, 2016.
Japanese Patent Application No. 2015-200279 Office Action dated Aug. 31, 2017.
Japanese Patent Application No. 2015-200279 Office Action dated Feb. 7, 2017.
Japanese Patent Application No. 2015-200279 Office Action dated Jul. 12, 2016.
Japanese Patent Application No. 2015-548762 Office Action dated Jul. 31, 2018.
Japanese Patent Application No. 2016-154639 Office Action dated Jun. 8, 2017.
Japanese Patent Application No. 2016-202835 Office Action dated Jun. 20, 2017.
Japanese Patent Application No. 2016-202835 Office Action dated Mar. 6, 2018.
Jasovský D, Littmann J, Zorzet A, Cars O. Antimicrobial resistance—a threat to the world's sustainable development. Upsala J Med Sci. 2016; 121: 159-64.
Johani K, Malone M, Jensen S et al. Microscopy visualisation confirms multi-species biofilms are ubiquitous in diabetic foot ulcers. Int Wound J. 2017; 14: 1160-9.
Jones et al., Antimicrobial activity of silver-containing dressings is influenced by dressing conformability with a wound surface. Wounds, 17:263-270 (2005).
JP-A-H7-504699 (English counterpart WO93/19152).
JP-A-H7-509236 (English counterpart WO94/02022).
Kapoor et al., Fluorescence and absorption spectra of Rose-Bengal dye in the presence of surfactants. Journal of Luminescence, 22(4): 429-439, 1981. (Abstract only).
Kaur et al., Effect of certain chelating agents on the antibacterial action of silver nitrate. Journal of Hygiene, Epidemiology, Microbiology and Immunology. 32(3): 299-306, 1988.
Keast D, Swanson T, Carville K, Fletcher J, Schultz G, Black J. Ten top tips . . . understanding and managing wound biofilm. Wounds International. 2014; 5: 20-3.
Kharkevich, D.A., Pharmacology: Textbook. Geotar-Media, p. 66-71, 2006.
Kim D, Namen W, Moore J, Buchanan M, Hayes V, Myntti M, Hakaim A. Clinical assessment of a biofilm-disrupting agent for the management of chronic wounds compared with standard of care: a therapeutic approach. Wounds. 2018 30: 120-30.
Kita et al., pH-Dependent preferential antibacterial activity of Ethylenediaminetetraacetic acid (EDTA). Japanese Journal of Bacteriology, 47(4):6 pages, 1992.
Kite et al., Use of in vivo-generated biofilms from hemodialysis catheters to test the efficacy of a novel antimicrobial catheter lock for biofilm eradication in vitro. J Clin Microbiol., 42.7 (2004): 3073-3076.
Kryukov et al., The role of bacteriological examination in diagnosis of chronic tonsillitis. Becthnk 3:35-38, 2008.
Lazarus G, Cooper D, Knighton D, Percoraro R, Rodeheaver G, Robson M. Definitions and guidelines for assessment of wounds and evaluation of healing. Wound Repair Regen. 1994; 2: 165-70.
Lewis K. Persister cells. Ann Rev Microbiol. 2010; 64: 357-72.
Lineaweaver et al., Topical antimicrobial toxicity. Arch Surg., 120(3):267-70 (1985).
Lipsky B, Aragón-Sánchez J, Diggle M et al. IWGDF guidance on the diagnosis and management of foot infections in persons with diabetes. Diabetes Metab Res Rev. 2016; 32: 45-74.
Lipsky B, Dryden M, Gottrup F et al. Antimicrobial stewardship in wound care: A position paper from the British society for antimicrobial chemotherapy and European wound management association. J. Antimicrob Chemother 2016; 71: 3026-35.
Lipsky B Medical treatment of diabetic foot infections. Clin Infect Dis. 2004; 39: S104-S114.
Lipsky B, Peters E, Senneville E et al. Expert opinion on the management of infections in the diabetic foot. Diabetes Metab Res Rev. 2012; 28(suppl 1): 163-78.
Macia M, Roho-Molinero E, Oliver A. Antimicrobial susceptibility testing in biofilm-growing bacteria. Clin Microbiol Infect. 2014; 20: 981-90.
Malone M, Bjarnsholt T, McBain A et al. The prevalence of biofilms in chronic wounds: a systematic review and meta-analysis of published data. J Wound Care. 2017; 26: 20-5.
McDonnell G, Russell A. Antiseptics and disinfectants: Activity, action, and resistance. Clin Microbiol Rev. 1999; 12: 147-79.
Meredith K, Burke N, Brownley H et al. Antimicrobial efficacy of enhanced and standard silver wound dressings in an in vitro mature bioburden model. Symposium on Advanced Wound Care. 2018 Poster presentation: Las Vegas.
Metcalf D, Bowler P. Biofilm delays wound healing: A review of the evidence. Burns Trauma. 2013; 1; 5-12.
Metcalf D, Bowler P. Clinical Impact of an enhanced antimicrobial dressing in non-healing wounds previously managed with antibiotics. Symposium on Advanced Wound Care. 2018 Poster presentation: Las Vegas.
Metcalf D, Bowler P, Parsons D. In: Dhanasekaran D, ed. Wound Biofilm and Therapeutic Strategies, Microbial Biofilms—Importance and Applications. Rijeka, Croatia: InTech; 2016. https://www.intechopen.com/books/microbial-importance-and-applications/wound-biofilm-and-therapeutic-strategies. Accessed Aug. 8, 2018.
Metcalf D, Parsons D, Bowler P. A next-generation antimicrobial wound dressing: a real-life clinical evaluation in the UK and Ireland. J Wound Care. 2016; 25: 132-8.
Mexican Patent Application No. MX/a/2013/006090 Official Action dated Jun. 7, 2016.
Muller et al. pH-dependent formation of ethylenediaminetetraacetic acid supramolecular aggregates. FEBS Lett 340: 17-21 (1994).
Nagai et al., Suppressive effects of EDTA for Pseudomonas aeruginosa products biofilm STN CAPLUS, Jan. 1, 1996, 1 page. XP002122029.
Nagoba B, Suryawanshi N, Wadher B, Selkar S. Acidic environment and wound healing: a review. Wounds. 2015; 27: 5-11.
Newman G, Walker M, Hobot J, Bowler P. Visualisation of bacterial sequestration and bactericidal activity within hydrating Hydrofiber wound dressings. Biomaterials. 2006; 27: 1129-39.
Nickel J, Wright J, Ruseska I, Marrie T, Whitfield C, Costerton J. Antibiotic resistance of pseudomonas aeruginosa colonizing a urinary catheter in vitro. Eur J Clin Microbiol. 1985; 4: 213-18.
Nix D, Pierce B, Haugen V. Eliminating non-compliance. In Bryant R and Nix D, eds. Acute and Chronic Wounds Current Management Concepts. 5th ed. St. Louis, MO: Elsevier; 2016: 428-40.
Nussbaum S, Carter M, Fife C et al. An economic evaluation of the impact, cost, and Medicare policy implications of chronic nonhealing wounds. Value Health. 2018; 21: 27-32.
Olsen I. Biofilm- specific antibiotic tolerance and resistance. Eur J Clin Microbiol Infect Dis. 2015; 34: 877-86.
Ono N. A Semi-quantitative measurement of glycocalyx and an ATP bioluminescent assay for the analysis of Pseudomonas Aeruginosa biofilm. The Japanese Journal of Urology, 86(9):1440-1449, 1995.
Ovington, The Value of Silver in Wound Management. Podiatry Today, Dec. 1999, 12(7):59-62. (marked as Exhibit 3 at the Deposition of Fiona Adam).
Parikh et al., Antimicrobial silver/sodium carboxymethyl cotton dressings for burn wounds Textile Research Journal, 75 (2):134-138 (2005).
Parsons et al., Enhanced Performance and Mode of Action of a Novel Antibiofilm Hydrofiber Wound Dressing. BioMed Research International 2016: ID 7616471:1-14 (2016).
PCT Patent Application No. PCT/GB2012/000329 International Search Report and Written Opinion dated Jul. 17, 2012.
PCT Patent Application No. PCT/US2014/038224 International Preliminary Report on Patentability dated Nov. 17, 2015.
PCT Patent Application No. PCT/US2014/038224 International Search Report dated Sep. 15, 2014.
PCT Patent Application No. PCT/US2014/038224 Written Opinion dated Sep. 15, 2014.

(56) References Cited

OTHER PUBLICATIONS

PCT Patent Application No. PCT/GB2006/004691 International Preliminary Report on Patentability dated Aug. 12, 2008.
PCT Patent Application No. PCT/GB2006/004691 International Search Report dated Jul. 7, 2008.
PCT Patent Application No. PCT/GB2006/004691 Written Opinion dated Jul. 7, 2008.
PCT Patent Application No. PCT/GB2009/002912 International Preliminary Report on Patentability dated Jun. 21, 2011.
PCT Patent Application No. PCT/GB2009/002912 International Search Report and Written Opinion dated Mar. 2, 2010.
PCT Patent Application No. PCT/GB2011/001665 International Preliminary Report on Patentability dated Jun. 4, 2013.
PCT Patent Application No. PCT/GB2011/001665 International Search Report dated Mar. 2, 2012.
PCT Patent Application No. PCT/GB2011/001665 Written Opinion dated Mar. 2, 2012.
Pennington JA., A review of iodine toxicity reports. J Am Diet Assoc., 90(11):1571-81 (1990).
Percival et al., Tetrasodium EDTA as a novel central venous catheter lock solution against biofilm DATA Biosis (online), Jun. 1, 2005, 6 pages XP002485725.
Percival S, Bowler P. Biofilms and their potential role in wound healing. Wounds. 2004; 16: 234-240.
Petchiappan A, Chatterji D. Antibiotic resistance: Current perspectives. ACS Omega 2017, 2, 7400-7409. https://www.researchgate.net/publication/321019969/download. Accessed Jul. 7, 2018.
Phillips T. Chronic cutaneous ulcers: Etiology and epidemiology. J Invest Dermatol. 1994; 102: 38S-41S.
Poon and Burd, In vitro cytotoxity of silver: implication for clinical wound care. Burns. 30(2):140-7 (2004).
Ramage et al., Inhibition on Candida albicans bioflim formation using divalent cation chelators (EDTA) Mycopathologia, Kluwer Academic Publishers, 164(6):301-306 (2007). XP019555313.
Reybrouck et al., Effect of ethylenediamine tetraacetate on the germicidal action of disinfectants against "Pseudomona." Acta Clinica Belgica, 24(1):32-41, 1969.
Rhoads D, Wolcott R, Percival S. Biofilms in wounds: management strategies. J Wound Care. 2008; 17: 502-9.
Rodeheaver G, Ratliff C. Wound cleansing, wound irrigation, wound disinfection. In: Krasner D, van Rijswijk L, eds. Chronic Wound Care: The Essentials e-Book. Malvern, PA: HMP; 2018: 47-62. Available at: https://s3.amazonaws.com/whywoundcare/Files/Chapter+5.pdf. Accessed Jul. 7, 2018.
Romanelli M, Vowden K, Weir D. Exudate management made easy. Wounds International. 2014. http://www.woundsinternational.com/made-easys/view/exudate-management-made-easy-1. Accessed Jul. 11, 2018.
Rondas A, Schols J, Stobberingh E, Price P. Definition of infection in chronic wounds by Dutch nursing home physicians. Int Wound J. 2006; 6: 267-74.
Russian Patent Application No. 2015153446 Office Action and Search Report dated Apr. 23, 2018.
Russian Patent Application No. 2013129866 Office Action dated Oct. 21, 2016.
Russian Patent Application No. 2013129866/10 Protocol of a Meeting with the Examiner dated Jun. 14, 2017.
Russian Patent Application No. 2013149176 Official Action dated Feb. 21, 2018.
Russian Patent Application No. 2013149176 Official Action dated Jun. 2, 2016.
Russian Patent Application No. 2015153446 Office Action dated Feb. 10, 2016 (In Russian).
Said et al., An in vitro test of the efficacy of an anti-biofilm wound dressing. Int J Pharm. 474(1-2):177-181 (2014).
Saudi Arabia Patent Application No. 515370133 2nd Examination Report dated Feb. 6, 2017.
Saudi Arabia Patent Application No. 515370133 Examination Report dated Oct. 18, 2016.

Savage V, Chopra I, ONeill A. *Staphylococcus aureus* biofilms promote horizontal transfer of antibiotic resistance. Antimicrob Agents Chemother. 2013; 57: 1968-70.
Sen C, Gordillo G, Roy S et al. Human skin wounds: A major and snowballing threat to public health and the economy. Wound Repair Regen. 2009; 17: 763-71.
Senter, A Textbook of Organic Chemistry, Fifth Ed. 1919, pp. 435-443.
Seth A, Zhong A, Nguyen K et al. Impact of a novel, antimicrobial dressing on in vivo, Pseudomonas aeruginosa wound biofilm: quantitative comparative analysis using a rabbit ear model. Wound Repair Regen. 2014; 22: 712-9.
Shanmugam V, Couch K, McNish S, Amdur R. Relationship between opioid treatment and rate of healing in chronic wounds. Wound Repair Regen. 2017; 25: 120-30.
Sharma et al., Toluidine blue-mediated photodynamic effects on Staphylococcal biofilms. Antimicrobial Agents and Chemotherapy, 52(1):299-305, 2008.
Smith and Nephew, OTC mediation information: Dermal wound cleanser—benzethonium chloride spray Dec. 17, 2009, p. 1-6. XP55031919.
Song T, Duperthuy M, Nyunt-Wai, S. Sub-optimal treatment of bacterial biofilms. Antibiotics. 2016; 5: 1-18.
Spellberg B, Srinivasan A, Chambers H. New societal approaches to empowering antibiotic stewardship. JAMA. 2016; 315: 1229-30.
Stevens D, Bisno A, Chambers H et al. Practice guidelines for the diagnosis and management of skin and soft tissue infections: 2014 update by the Infectious Diseases Society of America. Clin Infect Dis. 2014; 59: 147-59.
Chinese Patent Application No. 201180066375.2 Office Action dated Sep. 26, 2016.
Chinese Patent Application No. 201180066375.2 Reexamination Decision dated Dec. 20, 2017.
Chinese Patent Application No. 201280027537.6 Third Office Action dated Mar. 2, 2016.
Chinese Patent Application No. 201280027537.6 Decision of Reexamination dated Oct. 27, 2017.
Chinese Patent Application No. 201280027537.6 Office Action dated Sep. 12, 2016.
Chinese Patent Application No. 201480028155.4 Decision on Rejection dated Nov. 21, 2018.
Chinese Patent Application No. 201480028155.4 First Office Action dated Apr. 18, 2017.
Ciofu O, Rojo-Molinero E, Macia M, Oliver A. Antibiotic treatment of biofilm infections. APMIS. 2017; 125:304-19.
Costerton J, Geesey G, Cheng K. How bacteria stick. Sci Am. 1978; 238:86-95.
Costerton J, Irvin R, Cheng K. The bacterial glycocalyx in nature and disease. Ann Rev Microbiol. 1981; 35:299-324.
Costerton J, Stewart P, Greenberg E. Bacterial biofilms: a common cause of persistent infections. Science. 1999; 284: 1318-22.
Costerton JW. Bacterial biofilms in nature and disease. Ann Rev Microbiol. 1987; 41:435-64.
Database Biosis, Biosciences Information Service, Philadelphia, PA, 1992, Kida N., etaL, Effect of PH on Preferential Antibacterial Activity of Ethylenediaminetetraacetic Acid EDTA, XP002485724, Database Accession No. PREV199294118093.
Database Biosis, Biosciences Information Service, Philadelphia, PA, 2005, Percival, L, et al.. Effect of PH on Tetrasodium EDTA as a novel central venous catheter lock solution against biofilm, XP002485725, Database Accession No. PREV200600021247.
Database CA, Chemical Abstracts Service, Columbus, OH, US; Izzat, I.N., et al., Effect of varying concentrations of EDTA on the antimicrobial properties of cutting fluid preservatives, 1979, XP002485722, STN-International Database Accession No. 93:62380.
Database CA, Chemical Abstracts Service, Columbus, OH, US; Reybrouck, G., et al., Effect of ethylenediaminetetraacetate on the germicidal action of disinfectants against Pseudomonas aeruginosa, XP002485721, STN-International Database Accession No. 72:11588, 1969.
Database Medline, US National Library of Medicine, Bethesda, MD, 1988, Kaur, P., et al., Effect of certain chelating agents on the (56) References Cited

OTHER PUBLICATIONS antibacterial action of silver nitrate, XP002485723, STN-International Database Accession No. NLM3143759.

Demidova and Hamblin, Photodynamic therapy targeted to pathogens Int. J. Immunopathol Pharmacol., 17 (3):245-254, 2004.

Dini V, Salvo P, Janowska A, Di Francesco F, Barbini A, Romanelli M. Correlation between wound temperature obtained with an infrared camera and clinical wound bed score in venous leg ulcers. Wounds. 2015; 27:274-8.

Dougherty et al., Photodynamic therapy. Journal of the National Cancer Institute, 90(12):889-905, 1998.

Doughty D, Sparks B. Wound healing physiology and factors that affect the wound repair process. In Bryant R and Nix D, eds. Acute and Chronic Wounds: Current Management Concepts. 5th ed. St. Louis, MO: Elsevier; 2016:63-81.

Eming S, Martin P, Tomic-Canic M. Wound repair and regeneration: mechanisms, signaling, and translation. Sci Transl Med. 2014; 6: 57-72. doi: 10.1126/scitranslmed.3009337.

Etebu E, Arikekpar I. Antibiotics: Classification and mechanisms of action with emphasis on molecular perspective. Int J of Appl Microbiol and Biothech Res. 2016; 4:90-101. http://www.bluepenjournals.org/ijambr/pdf/2016/October/Etebu_and_Arikekpar.pdf. Accessed Aug. 8, 2018.

European Centre for Disease Prevention and Control (ECDC). Proposals for EU Guidelines on the Prudent Use of Antimicrobials in Humans. Stockholm: ECDC; 2017. http://ecdc.europa.eu/en/publications/_layouts/forms/Publication_DispForm.aspx?List=4f55ad51-4aed-4d32-b690-af70113dbb90&ID-1643. Accessed Jul. 2, 2018.

European Patent Application No. 09795521.5 Communication dated Mar. 24, 2017.

European Patent Application No. 09795521.5 Office Action dated May 9, 2018.

European Patent Application No. 12719420.7 Communication dated Jul. 20, 2016.

European Patent Application No. 12719420.7 Examination Report dated Apr. 5, 2017.

European Patent Application No. 12719420.7 Examination Report dated Aug. 7, 2018.

European Patent Application No. 14797983.5 Supplementary European Search Report dated Dec. 6, 2016.

European Patent Application No. 17163418.1 extended European Search Report dated Sep. 17, 2017.

European Patent Application No. 06820530.1 Communication dated Apr. 7, 2016.

European Patent Application No. 06820530.1 Communication dated Jan. 30, 2013.

European Patent Application No. 06820530.1 Communication dated Mar. 30, 2009.

FDA website on Medical Devices, Premarket Notification (510k), 4 pages, 2013.

Fife C, Carter M, Walker D, Thomson B. Wound care outcomes and associated cost among patients treated in US outpatient wound centers: Data from the US Wound Registry. Wounds. 2012; 24: 10-7.

Finnegan S, Percival S. EDTA: an antimicrobial and antibiofilm agent for use in wound care. Adv Wound Care. 2015; 4: 415-21.

Fleming D, Rumbaugh K. Approaches to dispersing medical biofilms. Microorganisms. 2017; 5: 1-16.

Frykberg R, Banks J. Challenges in the treatment of chronic wounds. Adv Wound Care. 2015; 4: 560-82.

Gardner S, Frantz R, Doebbeling B. The validity of the clincal signs and symptoms used to identify localized chronic wound infection. Wound Repair Regen. 2001; 9: 178-86.

Gardner S, Hillis S, Frantz R. Clinical signs of infection in diabetic foot ulcers with high microbial load. Biol Res Nurs. 2009; 11: 119-28.

Gilbert, et al., The Use of Poloxamer Hydrogels for the Assessment of Biofilm Suspectibility Towards Biocide Treatments, Journal of Applied Microbiology, 1998, 85: 985-990.

Gilchrist M, Seaton R. Outpatient parenteral antimicrobial therapy and antimicrobial stewardship: challenges and checklists. J Antimicrob Chemother. 2015; 70: 965-70.

Gottrup F. A specialized wound-healing center concept: importance of a multidisciplinary department structure and surgical treatment facilities in the treatment of chronic wounds. Am J Surg. 2004; 187: S38-S43.

Gottrup F, Apelqvist J, Bjarnsholt T et al. Antimicrobials and non-healing wounds: Evidence, controversies and suggestions—key messages. J Wound Care. 2014; 23: 477-8, 480, 482.

Guest JF, Vowden K. The health economic burden that acute and chronic wounds impose on an average clinical commissioning group/health board in the UK. J Wound Care. 2017; 26: 292-303.

Harding K, Szczepkowski M, Mikosiński J et al. Safety and performance evaluation of a next-generation antimicrobial dressing in patients with chronic venous leg ulcers. Int Wound J. 2016; 13: 442-8.

Harrison-Balestra et al., A wound isolated Pseudomonas aeruginosa grows a biofilm in vitro within 10 hours and is visualized by light microscopy. Dermatol. Surgery, 29(6): 631-635, 2003.

Hobot et al., Effect of Hydrofiber wound dressings on bacterial ultrastructure. J Electron Microsc (Tokyo). 50(2): 67-75 (2008).

Howell J, Stair T, Howell A, Mundt D, Falcone A, Peters S. The effect of scrubbing and irrigation with normal saline, povidone iodine, and cefazolin on wound bacterial counts in a Guinea pig model. Am J Emerg Med. 1993; 11: 134-38.

Stewart P. Antimicrobial tolerance in biofilms. Microbiol Spectrum. 2015; 3: 1-30. https://www.ncbi.nlm.nih.gov/pmc/articles/PMC4507308/pdf/nihms697879.pdf. Accessed Jul. 24, 2018.

Stotts R. Wound Bioburden. In Baranoski, S, Ayello, E. eds. Wound Care Essentials: Practice and Principles. Philadelphia, PA: Wolters Klower; 2004: 121-48.

Swisher, R.D., Surfactant effects on humans and other mammals. The Soap and Detergent Association, Scientific and Technical Report, 4:1-8, 11, 16, 17, 19, Nov. 1966.

Tallardia. Drug synergism: Its detection and applications. The Journal of Pharmacology and Experimental Therapeutics, 298(3):865-872, 2001.

Thomas and McCubbin, An in vitro analysis of the antimicrobial properties of 10 silver-containing dressings. The Journal of Wound Care, Sep. 2003, 12(8):105-108.

Thomas-Hess, C. Checklist for factors affecting wound healing. Adv Skin Wound Care. 2011; 24: 192.

Torkington-Stokes R, Metcalf D, Bowler P. Management of diabetic foot ulcers: valuation of case studies. Br J Nurs. 2016; 25: S27-S33.

Understanding biofilms. Bacteriality. Published online May 26, 2008. http://bacteriality.com/2008/05/biofilm/. Accessed Jul. 2, 2018.

United Nations. World Population Aging. New York. 2017. http://www.un.org/en/development/desa/population/publications/pdf/ageing/WPA2017_Highlights.pdf. Accessed Jul. 24, 2018.

U.S. Appl. No. 11/610,671 Office Action dated Apr. 2, 2008.
U.S. Appl. No. 11/610,671 Office Action dated Apr. 7, 2011.
U.S. Appl. No. 11/610,671 Office Action dated Aug. 17, 2009.
U.S. Appl. No. 11/610,671 Office Action dated Dec. 3, 2008.
U.S. Appl. No. 11/610,671 Office Action dated Feb. 18, 2010.
U.S. Appl. No. 11/610,671 Office Action dated Mar. 11, 2015.
U.S. Appl. No. 11/610,671 Office Action dated Mar. 20, 2014.
U.S. Appl. No. 11/610,671 Office Action dated Oct. 20, 2011.
U.S. Appl. No. 11/610,671 Office Action dated Oct. 8, 2014.
U.S. Appl. No. 11/610,671 Office Action dated Sep. 12, 2013.
U.S. Appl. No. 12/406,316 Office Action dated Apr. 4, 2012.
U.S. Appl. No. 12/406,316 Office Action dated Apr. 5, 2013.
U.S. Appl. No. 12/406,316 Office Action dated Aug. 10, 2011.
U.S. Appl. No. 12/406,316 Office Action dated Nov. 26, 2012.
U.S. Appl. No. 14/114,517 Office Action dated Aug. 13, 2015.
U.S. Appl. No. 13/990,755 Office Action dated Jan. 19, 2017.
U.S. Appl. No. 09/997,545 Office Action dated Feb. 10, 2003.
U.S. Appl. No. 09/997,545 Office Action dated Jul. 3, 2002.
U.S. Appl. No. 10/734,784 Office Action dated Apr. 4, 2007.
U.S. Appl. No. 13/124,472 Office Action dated Feb. 16, 2016.
U.S. Appl. No. 13/124,472 Office Action dated Jan. 18, 2013.
U.S. Appl. No. 13/124,472 Office Action dated Jun. 21, 2013.
U.S. Appl. No. 13/124,472 Office Action dated Jun. 4, 2015.

(56) References Cited

OTHER PUBLICATIONS

U.S. Appl. No. 13/124,472 Office Action dated Oct. 3, 2014.
U.S. Appl. No. 13/990,755 Office Action dated Jun. 29, 2017.
U.S. Appl. No. 13/990,755 Office Action dated May 5, 2016.
U.S. Appl. No. 14/114,517 Office Action dated Apr. 23, 2015.
U.S. Appl. No. 14/114,517 Office Action dated Mar. 24, 2016.
U.S. Appl. No. 14/114,517 Office Action dated Oct. 20, 2016.
U.S. Appl. No. 14/795,176 Office Action dated Feb. 3, 2016.
U.S. Appl. No. 14/889,818 Office Action dated Jan. 25, 2017.
Japanese Office Action; Japan Patent Office; Japanese Patent Application No. 2018-223751; dated Sep. 15, 2020; 4 pages.
PCT/GB2013/053374 International Preliminary Report on Patentability dated Jul. 2, 2015.
PCT/GB2013/053374 International Search Report dated Jul. 24, 2014.
PCT/GB2013/053374 Written Opinion dated Jul. 24, 2014.
PCT/US01/044773 International Search Report dated Aug. 31, 2001.
PCT/US01/044773 International Preliminary Report on Patentability completed Mar. 10, 2003.
Chinese Patent Application No. 201380073403.2 First Office Action dated Aug. 16, 2016.
European Patent Application No. 13821122.2 Communication dated Oct. 25, 2016.
Australian Patent Application No. 2013366038 Examination Report No. 1 dated Jun. 20, 2017.
Chinese Patent Application No. 201380073403.2 Office Action dated Jul. 3, 2017.
Chile Patent Application No. 3274-2015 Second Office Action dated Jan. 22, 2018.
Japanese Patent Application No. 2016-514095 Office Action dated Feb. 20, 2018.
U.S. Appl. No. 14/889,818 Office Action dated Jan. 10, 2018.
Australian Patent Application No. 2013366038 Examination Report No. 2 dated Jun. 19, 2018.
Australian Patent Application No. 2014265336 Examination Report No. 2 dated Mar. 26, 2018.
Chinese Patent Application No. 201380073403.2 Third Office Action dated Mar. 26, 2018.
Chinese Patent Application No. 201480028155.4 Office Action dated Mar. 22, 2018.
Mexican Patent Application No. MX/a/2015/015197 Office Action dated Mar. 2, 2018.
Taiwanese Patent Application No. 103117207 Office Action dated Apr. 11, 2018.
U.S. Appl. No. 14/889,818 Office Action dated Jun. 19, 2018.
510(k) Premarket Notification, AQUACEL and AQUACEL Ag, Section 5: 510(k) Summary revised Apr. 21, 2008, 6 pages.
AMR: a major European and Global challenge: fact sheet. Antimicrobial Resistance—European Commission (EC-AMR) 08, Sep. 2017. https://ec.europa.eu/health/amr/sites/amr/files/amr_factsheet_en.pdf. Accessed Jul. 2, 2018.
Anmar H, Dasgupta M, Costerton J. Testing the susceptibility of bacteria in biofilms to antibacterial agents. Antimicrob Agents Chemother. 1990, 34:2043-2046.
Arata, J. *Staphylococcus aureus* and the skin. Japanese Journal of Chemotherapy, 49(3):147-156, 2001.
Australian Patent Application No. 2014265336 Examiner's First Report dated Mar. 29, 2017.
Australian Patent Application No. 2017201084 Examination Report No. 1 dated May 18, 2018.
Banin et al., Chelator-induced dispersal and killing of Pseudomonas aeruginosa cells in a biofilm. Applied and Environmental Microbiology, 72(3):2064-2069, 2006.
Bay L, Kragh K, Eickhardt S, et al. Bacterial aggregates establish at the edges of acute epidermal wounds. Adv Wound Care. 2018; 7:105-13.
Bohn G, Liden B, Schultz G, et al. Ovine-based collagen matrix dressing: Next-generation callagen dressing for wound care. Adv Wound Care. 2016; 5:1-10.

Bowler et al., Dressing conformability and silver-containing wound dressings. Wounds U.K., 6:14-20 (2010).
Bowler P. Antibiotic resistance and biofilm tolerance: a combined threat in the treatment of chronic infections. J Wound Care. 2018 27:273-277.
Bowler P, Jones S, Davies B, Coyle E. Infection control properties of some wound dressings. J Wound Care. 1999; 8:499-502.
Bowler P, Jones S, Towers V, et al. Dressing conformability and silver-containing wound dressings. Wounds UK. 2010; 6:14-20.
Bowler P, Parsons D. Combatting wound biofilm and recalcitrance with a novel anti-biofilm Hydrofiber® wound dressing. Wound Medicine. 2016; 14:6-11.
Bryant R, Nix D. Principles for practice development to facilitate outcomes and productivity. In Bryant R and Nix D, eds. Acute and Chronic Wounds: Current Management Concepts. 5th ed. St. Louis, MO: Elsevier; 2016:1-20.
Canadian Patent Application No. 2,834,871 Office Action dated Oct. 1, 2018.
Canadian Patent Application No. 2,745,059 Office Action dated Apr. 20, 2018.
Canadian Patent Application No. 2,745,059 Office Action dated Aug. 2, 2017.
Canadian Patent Application No. 2,745,059 Office Action dated Oct. 25, 2016.
Canadian Patent Application No. 2,819,303 Office Action dated Oct. 24, 2017.
Canadian Patent Application No. 2,834,871 Office Action dated Jan. 31, 2018.
Capinera et al., Insectional activity of photoactive dyes to American and migratory grasshoppers (Orthoptera Acrididae). J. Econ. Entomol., 92(3):662-666, 2000.
Cavaliere R, Ball J, Turnbull L, Whitchurch C. The biofilm matrix destabilizers, EDTA and DNaseI, enhance the susceptibility of nontypeable Hemophilus influenzae biofilms to treatment with ampicillin and ciprofloxacin. Microbiology. 2014; 3:557-67.
Centers for Disease Control and Prevention. Antibiotic Resistance Threats in the United States. 2013. http://www.cdc.gov/drugresistance/threat-report-2013/pdf/ar-threats-2013-508.pdf. Accessed Aug. 1, 2018.
Ceri et al., The Calgary biofilm device: New technology for rapid determination of antibiotic susceptibilities of bacterial biofilms. Journal of Clinical Microbiology, 37(6):1771-1776, 1999.
Chan B, Cadarette S, Wodchis W, Wong J, Mittmann N, Kran M. Cost-of-illness studies in chronic ulcers: A systemic review. J Wound Care. 2017; 26:S4-S15.
Chemburu et al., Light-induced biocidal action of conjugated polyelectrolytes supported on colloids Langmuir, 24:11053-11062 (2008).
Chile Patent Application No. 3274-2015 Office Action dated Jun. 20, 2017.
U.S. Appl. No. 14/889,818 Office Action dated Jun. 9, 2017.
U.S. Appl. No. 14/889,818 Office Action dated Sep. 27, 2016.
U.S. Appl. No. 13/990,755 Office Action dated Apr. 5, 2018.
U.S. Appl. No. 15/372,299 Office Action dated Apr. 23, 2018.
Usacheva et al., Interaction of the photobactericides methylene blue and toluidine blue with a fluorophore in Pseudomonas aeruginosa cells. Lasers in Surgery and Medicine, 40:55-61, 2008.
Varani et al., Human skin in organ culture and human skin cells (keratinocytes and fibroblasts) in monolayer culture for assessment of chemically induced skin damage. Toxicol Pathol., 35(5):693-701, 2007.
Vengerovsky, A.I., Pharmaceutical incompatibility. Bulletin of Siberian Medicine, 3:12 pages, 2003. http.7lold.ssmu.ru/bull/03/3/1684.pdf.
Wainwright. Photodynamic antimicrobial chemotherapy (PACT). Journal of Antimicrobial Chemotherapy, 42:13-28, 1998.
Wainwright et al., The Use of new methylene blue in Pseudomonas aeruginosa biofilm destruction. Biofueling, 18:247-249, 2002. (Abstract only).
Walker M, Bowler P, Cochrane C. In vitro studies to show sequestration of matrix metalloproteinases by silver-containing wound care products. Ostomy Wound Manage. 2007; 53: 18-25.

(56) References Cited

OTHER PUBLICATIONS

Walker M, Metcalf D, Parsons D, Bowler P. A real-life clinical evaluation of a next-generation antimicrobial dressing on acute and chronic wounds. J Wound Care. 2015; 24: 11-22.

Webb R. A chronic case of confusion. J of Wound Care. 2017; 26: 421.

Welsby S. The Spectrum Activity of AQUACEL Ag+ with Strengthening Fibre Ribbon using an in Vitro Corrected Zone of Inhibition Assay. 2015. ConvaTec data on file.

White, "An historical overview of the use of silver in wound management," Actisorb Silver 220, The Silver Supplement Part Two: Clinical Evidence, 6 (Supp. Pt. 2): 6 pages (2001).

Wilkinson H, Stephenson C, Hardman M. Comparing the effectiveness of polymer debriding devices using a porcine wound biofilm model. Adv Wound Care. 2016; 5: 475-85.

Wirtanen, G. et al., Performance Evaluation of disinfectant Formulations Using Poloxamer-hydrogel Biofilm-constructs, Journal of Applied Microbiology, 1998, 85:965-971.

Wolcott R. Biofilms cause chronic infections. J of Wound Care. 2017; 26: 423-5.

Wolcott R. Disrupting the biofilm matrix improves wound healing outcomes. J Wound Care. 2015; 24: 366-71.

Wolcott R, Rhoads D. A study of biofilm-based wound management in subjects with critical limb ischemia. J Wound Care. 2008; 17: 145-55.

Wolcott R, Sanford N, Gabrilska R, Oates J, Wilkinson J, Rumbaugh K. Microbiota is a primary cause of pathogenesis of chronic wounds. J Wound Care. 2016; 25: Sup10: S33-S43.

Wood et al., Erythrosine is a potential photosensitizer for the photodynamic therapy of oral plaque biofilms. Journal of Antimicrobial Chemotherapy, 57:680-684, 2006.

Zölß C, Cech JD. Efficacy of a new multifunctional surfactant-based biomaterial dressing with 1% silver sulphadiazine in chronic wounds. Int Wound J. 2016; 13: 738-43. doi: 10.1111/iwj.12361.

Birttleness, Definition of Brittleness at Dictionary.com, https://www.dictionary.com/browse/brittleness, retrieved Sep. 25, 2019.

Sawhney, APS et al., Advent of Greige Cotton Non-Wovens Made using a Hydro-Entanglement Process, Textile Research Journal, vol. 80 (15), p. 1540-1549, 2010.

Australian Examination Report, Australian Patent Office, Australian Patent Application No. 2018204434, dated May 2, 2019, 4 pages.

Canadian Office Action, Canadian Intellectual Property Office, Canadian Patent Application No. 2,895,896, dated Dec. 13, 2019, 4 pages.

Japanese Office Action, Japan Patent Office, Japanese Patent Application No. 2018-223751, dated Nov. 5, 2019, 5 pages.

† cited by third party

PROCESSING OF CHEMICALLY MODIFIED CELLULOSIC FIBRES

CROSS-REFERENCE TO RELATED APPLICATIONS

This application is a continuation of U.S. patent application Ser. No. 14/654,498 filed Jun. 19, 2015, which is a U.S. National Phase application of International Patent Application Serial No. PCT/GB2013/053374 filed Dec. 20, 2013, which claims priority to Great Britain Patent Application Serial No. 1223408.4 filed Dec. 20, 2012, and Great Britain Patent Application Serial No. 1308774.7 filed May 15, 2013, the contents of each application are incorporated herein by reference in their entirety.

This invention relates to chemically modified cellulosic fibres and processes for making nonwoven fibre webs from them. In particular it relates to chemically modified cellulosic fibres which may be carded on a carding machine to produce a web. The fibres may be ultimately processed into nonwoven fabrics for instance by needling or entangling the web, the fabrics being suitable for use in absorbent personal products or absorbent medical products such as wound dressings. Also described are carding processes suitable for forming webs of chemically modified cellulosic fibres or blends of chemically modified fibres with other non-gelling fibres, for example viscose or Tencel or other cellulosic fibres.

Absorbent cellulosic fibres are well known. For instance GB-A-2220881 and GB-A-2094802 describe the production of carboxymethyl cellulose fibres from regenerated cellulose fibres (viscose rayon) fibres or from cotton. It is also known that carboxymethyl cellulose fibre of greater absorbency and strength can be produced from solvent-spun cellulose fibre. Such fibres are described in EP 0616650 and are manufactured by reacting solvent spun cellulose fibre with a strong alkali and a monochloroacetic acid reagent. It is also known that alternative chemical modification of cellulose fibres is possible and also has the effect of increasing the absorbency of the cellulose fibre. The cellulose fibre can for instance be modified by sulphonation, for example by substitution with an alkyl sulphonate at one or more of the hydroxyl groups on the anhydroglucose monomers that make up the cellulose backbone forming ether linkages. Modified cellulose of this type is known as cellulose sulphonate or cellulose alkyl sulphonate some of the insoluble forms of which are described in WO2012/061225.

Modifying the cellulose fibre requires the fibre to be exposed to one or more reagents which modify the cellulose by substitution, the degree of substitution determining the absorbency and solubility of the fibre. As the degree of substitution is increased the modified cellulose becomes increasingly soluble. As the solubility increases, absorbency also increases.

For some applications, for instance for absorbent gelling wound dressings, the chemically modified fibres need to be insoluble and retain some of their fibrous form when exposed to wound fluid and consequently a balance needs to be found between solubility and absorbency. The chemically modified fibre can be in the form of a tow, filament, sliver, yarn or staple fibre, woven, non-woven or knitted fabric.

Once the modification and neutralisation in acid has taken place, the fibres need to be washed to remove any unreacted alkali, chloroacetate, alkylsulphonate, other modifying agent or any by-products such as sodium chloride or sodium glycollate. An aqueous wash is generally used initially, preferably a mixture of water with a water-miscible organic solvent such as water and IMS, the major portion of the wash being organic solvent. The wash may contain an organic hydroxyl compound, a surfactant, and/or acid. The organic hydroxyl compound is a compound containing at least one alcoholic hydroxyl group, for example ethanol, methanol or another low molecular weight alcohol and/or a compound such as ethylene glycol or propylene glycol.

The final wash or finish typically comprises a large percentage of alcohol for instance, 99% industrial alcohol and 1% emulsifier or 100% alcohol. After washing, the fibres are dried at low temperature for instance as described in EP 0680344, by forced air drying or radiant heat drying.

As the washing step or steps to which the fibres are subjected following modification involve the use of relatively high percentages of organic solvents such as industrial alcohol, the drying of the fibres requires the solvents that are released to be managed from an environmental and safety perspective. It would be desirable to reduce the percentage of organic solvents used in the washing process so that environmental and safety standards can be readily met. There are also potential cost and efficiency advantages to using a lower percentage of organic solvents as the cost of materials and duty are reduced.

We have found that reducing, for instance, the percentage of organic solvent in the wash liquor used to wash modified cellulose fibres results in fibres that have a lower tensile strength making them less suitable for processing on textile machinery such as a carding machine. The lower tensile strength can lead to the problem of fibre breakage on carding which gives higher levels of airborne lint or dust (fly) and greater shedding of broken fibre from the finished fabric. The higher level of fly necessitates increased cleaning and environment management in the fabric production process which in turn increases cost. There is also more wastage in the process as fibres tend to drop out of the fabric during the process of manufacture.

Fibre breakage can also adversely affect the staple length which has the effect of reducing the strength of a carded web and nonwoven fabric made from the fibres. It is possible that fibre breakage leads to a failed card process where no non-woven mat is produced. A weaker product can be more difficult to remove from the wound as the integrity of the dressing can be compromised.

We have now found that it is possible to mitigate the problem of low tensile strength in modified fibres by controlled management of the moisture content of the fibres.

Accordingly the invention provides a chemically modified cellulosic web of fibres having a tensile strength of at least 3N per cm (N/cm) in the cross direction produced by processing fibres having a moisture content of at least 7% by weight.

Controlling the moisture content of the fibres, either by controlling the drying process following washing of the modified fibres as part of the chemical modification process or by conditioning the fibres to increase their moisture content to at least 7% subsequent to drying, increases the tensile strength of the fibres to the point where it is possible to process the fibres for example on a carding machine to produce a non-woven fibre web without the production of excessive fly or shedding from a fabric produced from the web. Preferably the moisture content of the fibres is kept at between 11 and 20% by controlling the drying process following washing of the modified fibres as part of the chemical modification process.

Preferably the tensile strength is measured in the cross direction on needled webs having a basis weight in the range of 80 to 120 gsm.

Accordingly the invention provides, in a further aspect, a process for producing a non-woven web of chemically modified cellulosic fibres comprising the steps of:
(i) obtaining chemically modified cellulosic fibres with a moisture content of at least 79%;
(ii) carding the fibres to make a nonwoven web of fibres.

The fibres are typically those resulting from a modification process using a wash or final rinse comprising less than 99% by weight such as 95% by weight of organic solvent in the wash liquor. By controlling the moisture content, the fibres can be processed into a consolidated form that allows a fabric to be produced by conventional carding means while mitigating the problem of fibre breakage and fly in the environment of the fabric production plant. A consolidated form could for example be a yarn, sliver, woven, non-woven or knitted fabric.

When the fibres are to be processed using textiling machinery, if it is found that the moisture content of the fibres is too low, the moisture content of the modified cellulosic fibres is increased by exposing the fibres to a moisture rich environment for at least 24 hours. Alternatively the drying of the fibres at the end of the chemical modification process can be controlled so that the moisture content of the fibres is maintained above 7% until the fibres are subjected to further processing such as with textiling machinery for instance by carding and needling.

Preferably the carded, needled fibre web has a tensile strength of from 3N/cm to 25N/cm, more preferably from 7N/cm to 25N/cm and most preferably from 10N/cm to 25N/cm.

The tensile strength of the carded, needled web is measured by cutting five specimens to a size of 25 mm×75 mm with the long dimension being in the direction to be tested. Tensile testing is carried out at a gauge length (effective test fabric length) of 50 mm. One end of the sample is fixed in an upper jaw of a tensile testing machine and allowed to dangle into the lower jaw. The sample is then fixed by closing the jaws without stretching the sample or allowing it to be slack. The crosshead speed is set to 100 mm/min and the sample pulled to break. The tensile strength is calculated by dividing the force at break by the sample width in cm.

Preferably the moisture content of the fibres prior to processing with textiling machinery is from 7% to 20% by weight and more preferably from 11% to 18%. More preferably the moisture content is from 11.5% and 15% by weight and most preferably it is between 12 and 15% by weight. A moisture content of 12.5% to 15% is particularly preferred and 15% is most preferred.

By the term moisture content is meant the amount of moisture (measured by weight) contained in the sample of fibres as a percentage of its conditioned weight and measured by the loss on drying.

The moisture content of the fibres is measured by calculating the loss on drying using a moisture balance operated in accordance with the instrument manual. For convenience, during the process for making the fibres, comparative measurements of moisture content can be made using a moisture meter for instance an Aquaboy (TEMI).

By the term carding in the present invention is meant a mechanical process that disentangles, cleans and intermixes fibres to produce a continuous web or sliver suitable for further processing.

In a further aspect of the invention, the invention provides a chemically modified cellulosic fibre having a moisture content of at least 7% by weight.

The invention will now be illustrated by the following examples.

EXAMPLE 1

Comparison of the moisture content of fibres vs their tensile strengths once carded and needled was made by measuring the initial moisture content of dried modified cellulosic fibres produced using washes of varying alcohol content. That initial moisture content was then increased by conditioning the fibres in a moist atmosphere for 24 hours at a relative humidity of 55 to 60% and the tensile strength of the needled fabric measured again.

Figure 1:
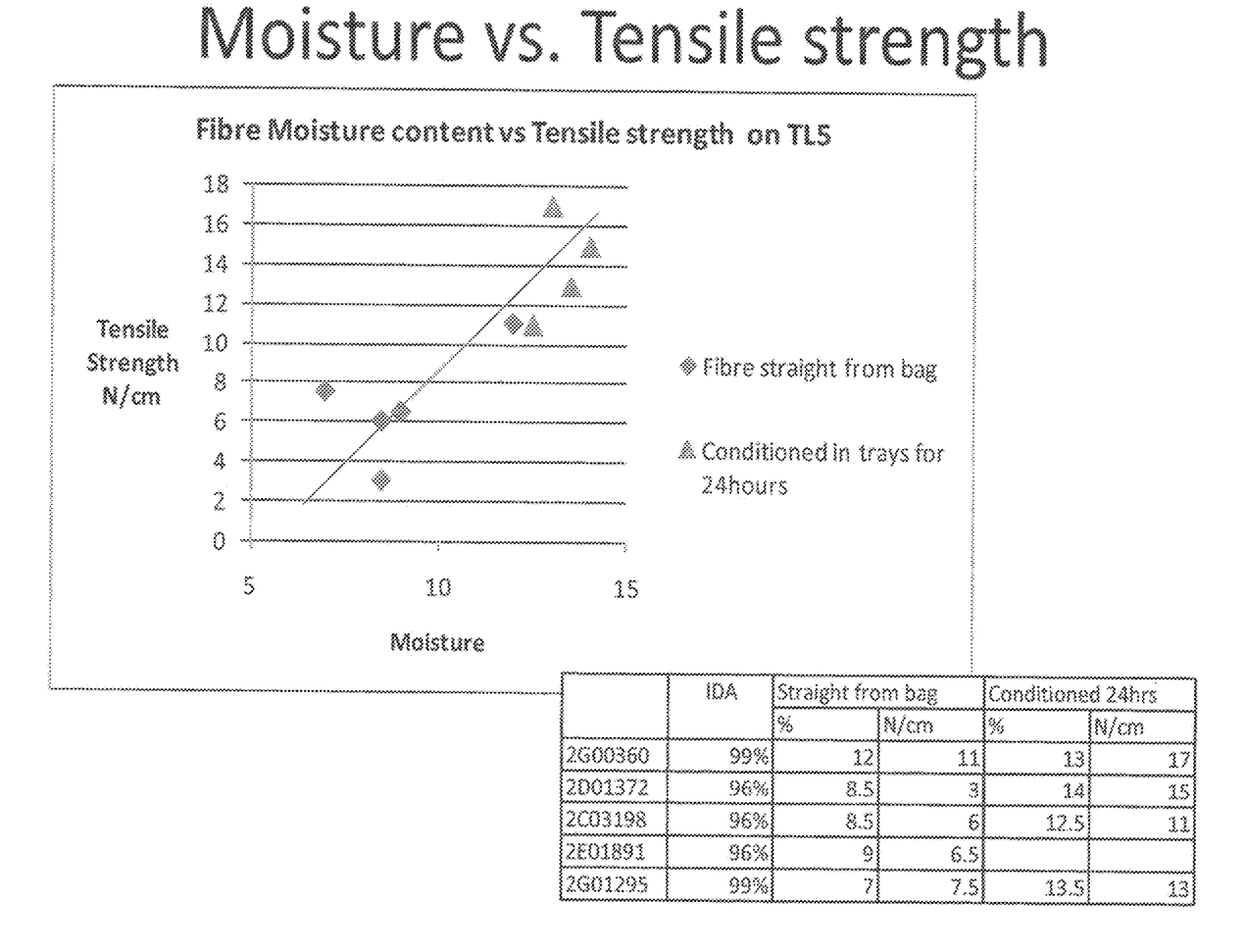
FIG. 1 shows the fiber moisture content vs. tensile strength of carded needled fabric in the transverse (cross) direction before and after moisture conditioning to increase moisture content.

FIG. 1 shows the fibre moisture content vs tensile strength of carded needled fabric in the transverse (cross) direction before and after moisture conditioning to increase the moisture content.

The results show that the moisture content of the fibres influences the tensile strength of the resulting carded and needled web. The column headed IDA in the table of FIG. 1 refers to the percentage of IDA (industrial denatured alcohols) used in the wash liquor as part of the modification process. The columns headed % refer to the % moisture in the fibre and N/cm to the tensile strength of the resulting carded needled web in the transverse direction. It can be seen from FIG. 1 that decreasing the % of IDA in the wash liquor has a negative influence on tensile strength for carded and needled webs made from unconditioned fibres. It can also be seen that once the moisture content of those fibres is raised to more than 11%, such as 12.5 to 14% moisture those tensile strength values of the carded needled web increase.

EXAMPLE 2

Effect of moisture content on the tensile strength of silver containing wound dressings.

Dressings were prepared by modification of solvent spun cellulose tow to a degree of substitution of 0.3 to form carboxymethylcellulose, neutralising to a pH of 5.5 with an organic acid. Adding 1.2% cationic silver by an ion exchange process in a largely organic solvent such as by the process described in Ep1343510, washing in an aqueous organic solution containing sodium chloride and di-sodium EDTA for light stabilisation and to entrain approximately 0.4% EDTA. Followed by washing in organic solvent wash containing fibre finishing agents including tween 20 and benzethonium chloride (to give 0.135% wt/wt BeCl on the finished product) and subsequently warm air drying, cutting to staple and processing into a nonwoven felt by carding and a needle punching process. The dressings were cut to size from the web and packaged in a light, moisture and vapour impermeable heat sealed foil pouch.

The dressings were removed from the packs and then subjected to various controlled environments.

Controlled Environments

Ambient as packed, tested without any preconditioning
Zero humidity: Stored in a square desiccator with 3 perforated perspex shelves above a layer of silica gel desiccant, conditioned for a minimum of 5 days
25° C./60% RH, for a minimum of 6 days
30° C./65% RH, for a minimum of 6 days 40° C./75% RH, for a minimum of 6 days Samples (ambient as packed) were tested immediately after opening the packs. Samples removed from the other environments were sealed into plastic bags during removal, and then tested immediately. The plastic bags (also preconditioned in corresponding controlled environments) were used to maintain the humidity of the environment of the samples until the point of testing.

Loss on Drying CLOD)

LOD of the samples was determined using the Ohaus moisture balance MB23 operated in accordance with the instruction manual. A sample mass of greater than 1 gram was used. Samples were cut to fit within the weighing pan, ensuring there was adequate clearance from the heating element. A standardised method was used with a maximum temperature limit of 110° C. The endpoint was determined automatically when the sample mass stopped reducing and was stable. Under these conditions the fabric did not char. Typically, samples would be subjected to a 10 minute cycle.

Fabric Thickness (Loft)

Samples were tested using the Hampden Soft Materials Thickness Gauge, Model FMTml-4D, S/N 14082. Fabric thickness (sometimes referred to as loft) was determined for 6 dressings per batch.

Fabric Dry Tensile Strength 2.5 cm×7.5 cm rectangular strips were cut from along the length (machine direction) and across the width (transverse direction) using a ribbon cutting die and press. Samples were conditioned as described Table 1. The peak force and the extension at which that force occurred were recorded when a 50 mm test length was stretched at a constant separation rate of 100 mm per minute.

Results

TABLE 1

Relationship between absolute and relative humidity

| Conditioning | Dry | Ambient | 25° C./ 60% RH | 30° C./ 65% RH | 40° C./ 75% RH |
|---|---|---|---|---|---|
| Moisture (g/m3) | 0.00 | 9.50 | 13.81 | 19.71 | 38.29 |
| Thickness (mm) | 0.170 | 0.190 | 0.198 | 0.183 | 0.202 |
| LOD % | 9.28 | 11.93 | 14.17 | 15.27 | 18.10 |
| Tensile Machine (N/cm) | 3.10 | 5.19 | 5.80 | 5.36 | 7.75 |
| Tensile Transverse (N/Cm) | 5.15 | 6.53 | 11.12 | 10.23 | 14.28 |
| GSM (g/m2) | 91 | 102 | 105 | 98 | 108 |

Loss on drying is the summation of all the volatile substances that can be removed by heating at 110° C. These include ethanol, water and to some degree acetic acid.

For this particular fibre, for this example, textile trials have shown that fibres for use in wound dressings according to the invention can be successfully textiled between 42% and 50% RH at around 18 to 20° C. Trials suggest that fibres with 10.5% to 11.5% w/w moisture content can be carded efficiently.

The results show that tensile strength, loft and LOD are all functions of equilibrium moisture content. The results suggest that fibres with a moisture content of greater than 9% will be able to be textiled to produce dressings suitable for use in the present invention.

EXAMPLE 3

Materials

Two gelling fibre types were used in this study; cellulose ethylsulphonate (CES) and carboxymethyl cellulose (CMC).

TABLE 1

Surnmary of gelling fibres used

| Gelling Fibre |
|---|
| CES fibre tow |
| CMC fibre tow |

Methods

Single fibres were mounted onto card windows as described in BS EN 5079:1996.

In addition, tow bundles were prepared to assess the moisture content.

Fibres were oven dried at 105° C. for one hour prior to being conditioned at the chosen relative humidity for a minimum of 16 hours. The mass of the oven dried tow bundles (W1) and the conditioned tow bundles (W2) was taken to assess the moisture content of the fibres, using Equation 1.

$$\text{Moisture Content (\%)} = \frac{W2 - W1}{W2} \times 100 \qquad \text{Equation 1}$$

Single fibre tensile strength of the conditioned samples was undertaken using the method described in BS EN 5079:1996.

Fibres were tested at 45% RH, 65% RH, and 85% RH.

Results

Results found that a significantly higher (P≤0.05) tensile strength was seen in the samples conditioned at 65% RH than those conditioned at 45% RH and 85% RH as shown in Table 2.

TABLE 2

Summary of results

| | Relative Humidity of Atmosphere (%) Ambient | 45 | 65 | 85 |
|---|---|---|---|---|
| CES | Moisture Content in fibre (%) w/w | 9 | 15 | 22 |
| | Mean Fibre Breaking Strength (cN) | 4.85 | 6.16 | 3.79 |
| | Standard Deviation (cN) | 1.08 | 3.61 | 1.21 |
| | T-Test aganst 65% RH data P value | 0.016 | N/A | 0.000 |
| CMC | Moisture Content in fibre (%) w/w | 12 | 15 | 21 |
| | Mean Fibre Breaking Strength (cN) | 6.04 | 3.24 | 4.16 |
| | Standard Deviation (cN) | 2.65 | 6.06 | 1.55 |
| | T-Test against 65% RH data P value | 0.029 | N/A | 0.000 |

The invention claimed is:

1. A process for processing a cellulosic fibre or a cellulosic filament, the process comprising:
   chemically modifying the cellulose of the cellulosic fibre or the cellulosic filament by substitution to increase absorbency;
   washing the chemically modified cellulosic fibre or chemically modified cellulosic filament in a wash solution comprising up to 99% by weight of an organic solvent and at least 95% by weight of the organic solvent; and adjusting the washed fibre or washed filament to a moisture content of at least 7% by weight.

2. The process of claim 1, wherein the washed fibre or washed filament is dried to a moisture content from 11% to 18% by weight.

3. The process of claim 1, wherein the adjusting step comprises drying the washed fibre or washed filament.

4. The process of claim 3, further comprising carding the dried fibre or dried filament to make a nonwoven web of fibre.

5. The process of claim 4, further comprising needling the nonwoven web of fibre to form a wound dressing.

6. The process of claim 5, further comprising sealing the wound dressing in a pouch that maintains the moisture content of the wound dressing in a sterile environment.

7. The process of claim 1, wherein the adjusting step comprises conditioning the washed fibre or washed filament in an atmosphere having a relative humidity of at least 40%.

8. The process of claim 7, wherein the relative humidity is from 45% to 85%.

9. The process of claim 7, further comprising carding the conditioned fibre or filament to produce a non-woven web of chemically modified cellulosic fibre.

10. A process for producing a non-woven web of chemically modified cellulosic fibres, the process comprising:
    neutralizing chemically modified cellulosic fibres;
    finishing the chemically modified cellulosic fibres with a solution comprising less than 99% by weight of an organic solvent to produce finished chemically modified cellulosic fibres;
    adjusting the moisture content of the finished chemically modified cellulosic fibres to a moisture content from 11% to 20% by weight;
    processing the finished chemically modified cellulosic fibres into the non-woven web of chemically modified cellulosic fibres, and wherein the moisture content of the non-woven web of chemically modified cellulosic fibres is from 11% to 20% by weight; and
    packaging the non-woven web of chemically modified cellulosic fibres in a pouch that maintains the moisture content of the non-woven web of chemically modified cellulosic fibres in a sterile environment, and wherein the packaged non-woven web of chemically modified cellulosic fibres has a tensile strength of at least 3N per cm,
    wherein the solution comprises at least 95% by weight of the organic solvent.

11. The process of claim 10, wherein the solution comprises less than 95% by weight of an organic solvent.

12. The process of claim 10, wherein the adjusting step comprises drying the finished chemically modified cellulosic fibres to achieve the moisture content from 11% to 20% by weight.

13. The process of claim 10, wherein the adjusting step comprises conditioning the finished chemically modified cellulosic fibres in air having a relative humidity of at least 40% to achieve the moisture content from 11% to 20% by weight.

14. The process of claim 13, wherein the relative humidity is from 45% to 85%.

15. The process of claim 10, wherein the adjusting step comprises drying the finished chemically modified cellulosic fibres in air having a relative humidity of at least 40% to achieve the moisture content from 11% to 20% by weight.

16. A non-woven web of chemically modified cellulosic fibres produced by the process of claim 10.

17. The non-woven web of chemically modified cellulosic fibres of claim 16, wherein the non-woven web of chemically modified cellulosic fibres has a tensile strength from 3N/cm to 25N/cm.

18. The non-woven web of chemically modified cellulosic fibres of claim 16, wherein the non-woven web of chemically modified cellulosic fibres has a basis weight from 80 gsm to 120 gsm.

19. The non-woven web of chemically modified cellulosic fibres of claim 16, wherein the tensile strength is in a cross-direction.

* * * * *